(12) United States Patent
Sakaguchi et al.

(10) Patent No.: US 6,673,913 B1
(45) Date of Patent: Jan. 6, 2004

(54) GANP PROTEINS

(75) Inventors: Nobuo Sakaguchi, Kumamoto (JP); Kazuhiko Kuwahara, Kumamoto (JP)

(73) Assignee: Kumamoto Technology & Industry Foundation, Kumamoto (JP)

( * ) Notice: Subject to any disclaimer, the term of this patent is extended or adjusted under 35 U.S.C. 154(b) by 0 days.

(21) Appl. No.: 09/914,272

(22) PCT Filed: Aug. 27, 2000

(86) PCT No.: PCT/JP99/04634

§ 371 (c)(1), (2), (4) Date: Dec. 5, 2001

(87) PCT Pub. No.: WO00/50611

PCT Pub. Date: Aug. 31, 2000

(30) Foreign Application Priority Data

Feb. 24, 1999 (JP) .............................................. 11-47035

(51) Int. Cl.[7] .......................... C07H 21/04; C07K 1/00; C12N 9/12; C12N 15/00; C12N 5/00
(52) U.S. Cl. .................. 536/23.2; 435/194; 435/320.1; 435/252.3; 435/325; 530/350
(58) Field of Search .............................. 435/194, 252.3, 435/320.1, 325; 530/350; 536/23.2

(56) References Cited

PUBLICATIONS

Nagase et al., DNA Res., 5. 31–39, 1998.*
International Search Report prepared by Japanese Patent Office.
Thomas Christoph., et al., "M17: a novel gene expressed in germinal centers", International Immunology (1994), vol. 6, No. 8, pp. 1203–1211.
Ming–Jie Li, et al., "Rad51 expressio and localization in B cells carrying out class switch recombination", Proc. Natl. Acad. Sci. USA (1996), vol. 93, No. 19, pp. 10222–10227.
Frank C. Kuo et al.,"Augmented expression of a human gene for 8–oxoguanine DNA glycosylase in B lymphocytes of the dark zone in lymph node germinal centers", J. Exp. Med. (1997), vol. 176, No. 9, pp. 1547–1556.
Masaki Hikida, et al., "Reexpression of RAG–1 and RAG–2 genes in activated mature mouse B cells", Science (1996), vol. 274, No. 5295, p. 2092–2094.
Shuhua Han., et al., "Neoteny in lymphocytes: Rag1 and Rag2 expression in germinal center B cells", Science (1996), vol. 274, No. 5295, pp. 2094–2097.
Kazuhiko Kuwahara, et al., "Identification of a 52–kDa molecule coprecipitated with the Ig receptor–related MB–1 protein that is inducibly phosphorylated by the stimulation with phorbol myristate acetate", J. Immunol. (1994), vol. 152, pp. 2742–2452.

* cited by examiner

*Primary Examiner*—Maryam Monshipouri
(74) *Attorney, Agent, or Firm*—McDermott, Will & Emery

(57) ABSTRACT

The object of the present invention is to provide a novel protein having a kinase activity and a gene encoding said protein. According to the present invention, there is provided a GANP protein which is represented by the amino acid sequence shown in SEQ ID No. 1 or No. 3 of the sequence listing, and is involved in the signal conversion of abnormal B cell differentiation in an autoimmune state, and has a kinase activity, and a polynucleotide which encodes the protein.

6 Claims, 23 Drawing Sheets

GANP antigen expressed in PNA+ cells
at the distal part of GCs
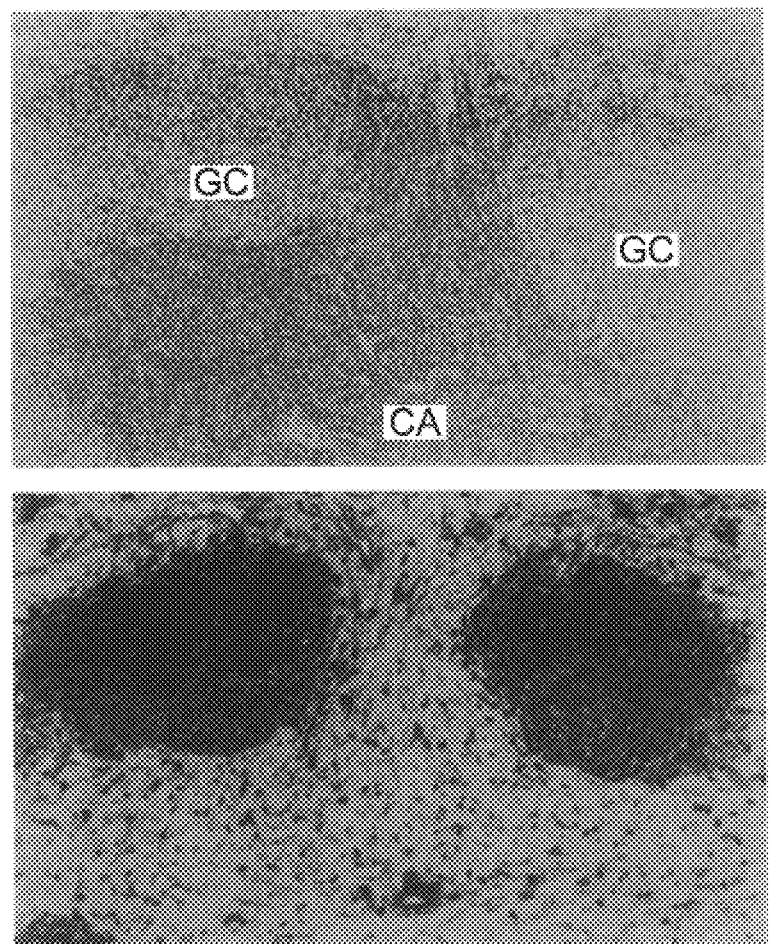
29-15 (blue), PNA (brown), Anti-BrdU (red),
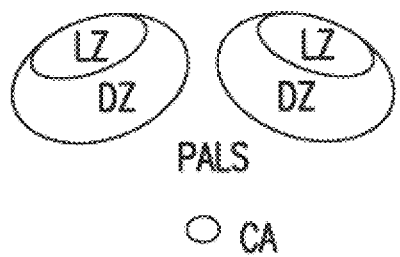
FIG.3

29-15 (blue)
PAS staining

```
MHPVNPFGGS  SPSAFAVSSS  TTGTYQTKSP  FRFGQPSLFG  QNSTPSKSLA   50
FSQVPSFATP  SGGSHSSSLP  AFGLTQTSSV  GLFSSLESTP  SFAATSSSSV  100
PGNTAFSFKS  TSSVGVFPSG  ATFGPETGEV  AGSGFRKTEF  KFKPLENAVF  150
KPIPGPESEP  EKTQSQISSG  FFTFSHPVGS  GSGGLTPFSF  PQVTNSSVTS  200
SSFIFSKPVT  SNTPAFASPL  SNQNVEEEKR  VSTSAFGSSN  SSFSTFPTAS  250
PGSLGEPFPA  NKPSLRQGCE  EAISQVEPLP  TLMKGLKRKE  DQDRSPRRHC  300
HEAAEDPDPL  SRGDHPPDKR  PVRLNRPRGG  TLFGRTIQEV  FKSNKEAGRL  350
GSKESKESGF  AEPGESDHAA  VPGGSQSTMV  PSRLPAVTKE  EEESRDEKED  400
SLRGKSVRQS  KRREEWIYSL  GGVSSLELTA  IQCKNIPDYL  NDRAILEKHF  450
SKIAKVQRVF  TRRSKKLAVI  HFFDHASAAL  ARKKGKGLHK  DVVIFWHKKK  500
ISPSKKLFPL  KEKLGESEAS  QGIEDSPFQH  SPLSKPIVRP  AAGSLLSKSS  550
PVKKPSLLKM  HQFEADPFDS  GSEGSEGLGS  CVSSLSTLIG  TVADTSEEKY  600
RLLDQRDRIM  RQARVKRTDL  DKARAFVGTC  PDMCPEKERY  LRETRSQLSV  650
FEVVPGTDQV  DHAAAVKEYS  RSSADQEEPL  PHELRPSAVL  SRTMDYLVTQ  700
IMDQKEGSLR  DWYDFVWNRT  RGIRKDITQQ  HLCDPLTVSL  IEKCTRFHIH  750
CAHFMCEEPM  SSFDAKINNE  NMTKCLQSLK  EMYQDLRNKG  VFCASEAEFQ  800
GYNVLLNLNK  GDILREVQQF  HPDVRNSPEV  NFAVQAFAAL  NSNNFVRFFK  850
LVQSASYLNA  CLLHCYFNQI  RKDALRALNV  AYTVSTQRST  VFPLDGVVRM  900
LLFRDSEEAT  NFLNYHGLTV  ADGCVELNRS  AFLEPEGLCK  ARKSVFIGRK  950
LTVSVGEVVN  GGPLPPVPRH  TPVCSFNSQN  KYVGESLATE  LPISTQRAGG 1000
DPAGGGRGED  CEAEVDLPTL  AVLPQPPPAS  SATPALHVQP  LAPAAAPSLL 1050
QASTQPEVLL  PKPAPVYSDS  DLVQVVDELI  QEALQVDCEE  VSSAGAAYVA 1100
AALGVSNAAV  EDLITAATTG  ILRHVAAEEV  SMERQRLEEE  KQRAEEERLK 1150
QERELMLTQL  SEGLAAELTE  LTVTECVWET  CSQELQSAVK  IDQKVRVARC 1200
CEAVCAHLVD  LFLAEEIFQT  AKETLQELQC  FCKYLQRWRE  AVAARKKFRR 1250
QMRAFPAAPC  CVDVNDRLQA  LVPSAECPIT  EENLAKGLLD  LGHAGKVGVS 1300
CTRLRRLRNK  TAHQIKVQHF  HQQLLRNAAW  APLDLPSIVS  EHLPMKQKRR 1350
FWKLVLVLPD  VEEQTPESPG  RILENWLKVK  FTGDDSMVGD  IGDNAGDIQT 1400
LSVFNTLSSK  GDQTVSVNVC  IKVAHGTLSD  SALDAVETQK  DLLGTSGLML 1450
LLPPKVKSEE  VAEEELSWLS  ALLQLKQLLQ  AKPFQPALPL  VVLVPSSRGD 1500
SAGRAVEDGL  MLQDLVSAKL  ISDYIVEIP   DSVNDLQGTV  KVSGAVQWLI 1550
SGCPQALDFC  CQTLVQYVED  GISREFSRRF  FHDRRERRLA  SLPSQEPSTI 1600
IELFNSVLQF  LASVVSSEQL  CDISWPVMEF  AEVGGSQLLP  HLHWNSPEHL 1650
AWLKQAVLGF  QLPQMDLPPP  GAPWLPVCSM  VIQYTSQIPS  SSQTQPVLQS 1700
QAENLLCRTY  QKWKNKSLSP  GQELGPSVAE  IPWDDIITLC  INHKLRDWTP 1750
PRLPVTLEAL  SEDGQICVYF  FKNLLRKYHV  PSSWEQARMQ  TQRELQLSHG 1800
RSGMRSIHPP  TSTFPTPLLH  VHQKGKKKEE  SGREGSLSTE  DLLRGASAEE 1850
LLAQSLSSSL  LEEKEENKRF  EDQLQQWLSQ  DSQAFTESTR  LPLYLPQTLV 1900
SFPDSIKTQT  MVKTSTSPQN  SGTKQLRFS   EASGSSLTEK  LKLLERLIQS 1950
SRAEEAASEL  HLSALLEMVD  M
```

FIG.9

Increased expression of GANP antigen
by mitogenic stimulation *in vitro*
cytoplasma stainning
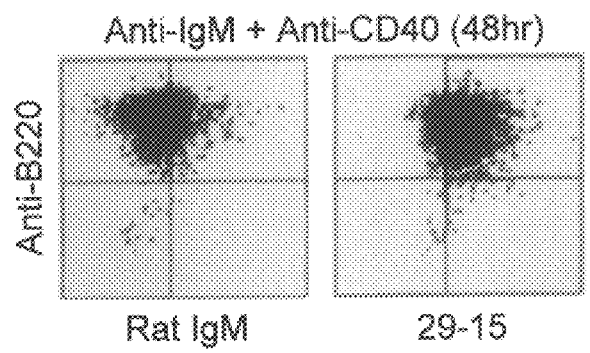
Immuno stainning
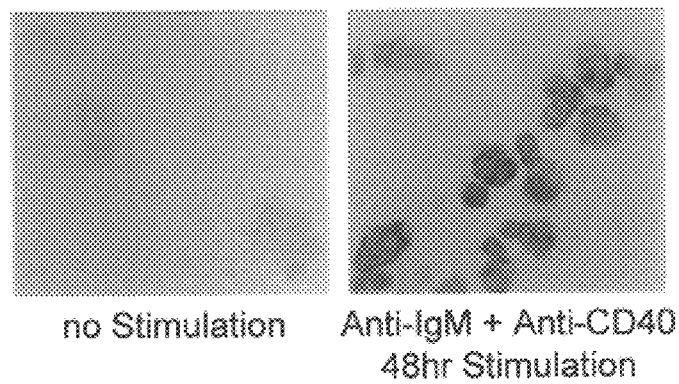
FIG.13

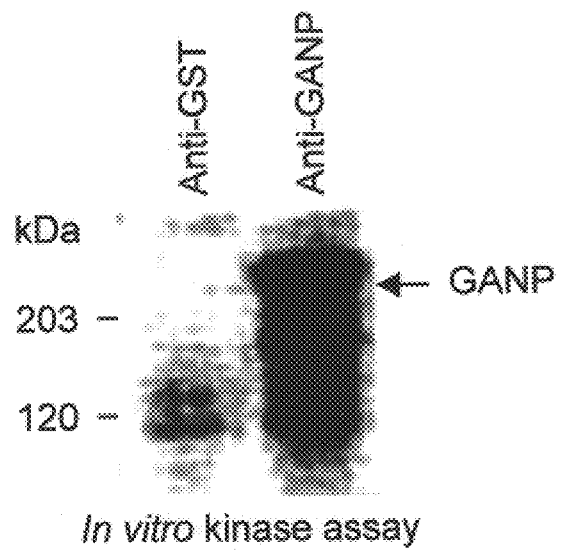
*In vitro* kinase assay
FIG. 14A
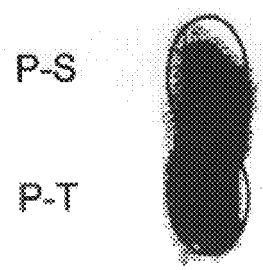
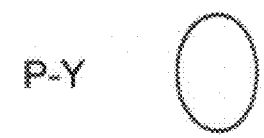
phospho amino acid analysis
FIG. 14B

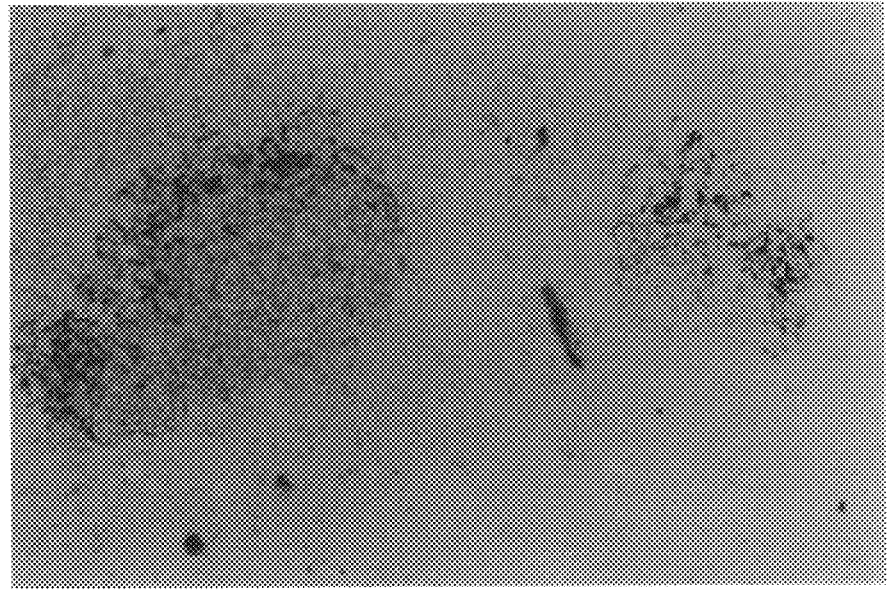
Anti-MCM3 (blue)
Anti-CR1 (brown)
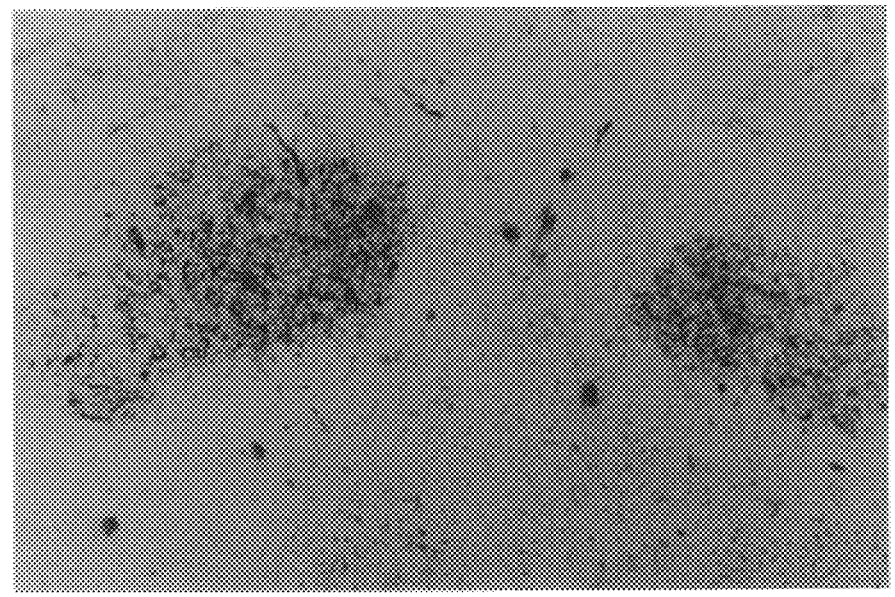
Anti-MCM3 (blue)
PNA (brown)
FIG.20

```
         10          20          30          40          50          60
MNPTNPFSGQ  QPSAFSASSS  NVGTLPSKPP  FRFGQPSLFG  QNSTLSGKSS  GFSQVSSFPA 70          80          90         100         110         120
SSGVSHSSSV  QTLGFTQTSS  VGPFSGLEHT  STFVATSGPS  SSSVLGNTGF  SFKSPTSVGA 130         140         150         160         170         180
FPSTSAFGQE  AGEIVNSGFG  KTEFSFKPLE  NAVFKPILGA  ESEPEKTQSQ  IASGFFTFSH 190         200         210         220         230         240
PISSAPGGLA  PFSFPQVTSS  SATTSNFTFS  KPVSSNNSLS  AFTPALSNQN  VEEEKRGPKS 250         260         270         280         290         300
IFGSSNNSFS  SFPVSSAVLG  EPFQASKAGV  RQGCEEAVSQ  VEPLPSLMKG  LKRKEDQDRS 310         320         330         340         350         360
PRRHGHEPAE  DSDPLSRGDH  PPDKRPVRLN  RPRGGTLFGR  TIQDVFKSNK  EVGRLGNKEA 370         380         390         400         410         420
KKETGFVESA  ESDHMAIPGG  NQSVLAPSRI  PGVNKEEETE  SREKKEDSLR  GTPARQSNRS 430         440         450         460         470         480
ESTDSLGGLS  PSEVTAIQCK  NIPDYLNDRT  ILENHFGKIA  KVQRIFTRRS  KKLAVVHFFD 490         500         510         520         530         540
HASAALARKK  GKSLHKDMAI  FWHRKKISPN  KKPFSLKEKK  PGDGEVSPST  EDAPFQHSPL 550         560         570         580         590         600
GKAAGRTGAS  SLLNKSSPVK  KPSLLKAHQF  EGDSFDSASE  GSEGLGPCVL  SLSTLIGTVA 610         620         630         640         650         660
ETSKEKYRLL  DQRDRIMRQA  RVKRTDLDKA  RTFVGTCLDM  CPEKERYMRE  TRSQLSVFEV 670         680         690         700         710         720
VPGTDQVDHA  AAVKEYSRSS  ADQEEPLPHE  LRPLPVLSRT  MDYLVTQIMD  QKEGSLRDWY 730         740         750         760         770         780
DFVWNRTRGI  RKDITQQHLC  DPLTVSLIEK  CTRFHIHCAH  FMCEEPMSSF  DAKINNENMT 790         800         810         820         830         840
KCLQSLKEMY  QDLRNKGVFC  ASEAEFQGYN  VLLSLNKGDI  LREVQQFHPA  VRNSSEVKFA 850         860         870         880         890         900
VQAFAALNSN  NFVRFFKLVQ  SASYLNACLL  HCYFSQIRKD  ALRALNFAYT  VSTQRSTIFP 910         920         930         940         950         960
LDGVVRMLLF  RDCEEATDFL  TCHGLTVSDG  CVELNRSAFL  EPEGLSKTRK  SVFITRKLTV 970         980         990        1000        1010        1020
SVGEIVNGGP  LPPVPRHTPV  CSFNSQNKYI  GESLAAELPV  STQRPGSDTV  GGGRGEECGV 1030        1040        1050        1060        1070        1080
EPDAPLSSLP  QSLPAPAPSP  VPLPPVLALT  PSVAPSLFQL  SVQPEPPPPE  PVPMYSDEDL 1090        1100        1110        1120        1130        1140
AQVVDELIQE  ALQRDCEEVG  SAGAAYAAAA  LGVSNAAMED  LLTAATTGIL  RHIAAEEVSK 1150        1160        1170        1180        1190        1200
ERERRREQERQ RAEEERLKQE  RELVLSELSQ  GLAVELMERV  MMEFVRETCS  QELKNAVETD 1210        1220        1230        1240        1250        1260
QRVRVARCCE  DVCAHLVDLF  LVEEIFQTAK  ETLQELQCFC  KYLQRWREAV  TARKKLRRQM
```

FIG.21A

```
          1270       1280       1290       1300       1310       1320
    RAFPAAPCCV DVSDRLRALA PSAECPIAEE NLARGLLDLG HAGRLGISCT RLRRLRNKTA 1330       1340       1350       1360       1370       1380
    HQMKVQHFYQ QLLSDVAWAS LDLPSLVAEH LPGRQEHVFW KLVLVLPDVE EQSPESCGRI 1390       1400       1410       1420       1430       1440
    LANWLKVKFM GDEGSVDDTS SDAGGIQTLS LFNSLSSKGD QMISVNVCIK VAHGALSDGA 1450       1460       1470       1480       1490       1500
    IDAVETQKDL LGASGLMLLL PPKMKSEDMA EEDVYWLSAL LQLKQLLQAK PFQPALPLVV 1510       1520       1530       1540       1550       1560
    LVPSPGGDAV EKEVEDGLML QDLVSAKLIS DYTVTEIPDT INDLQGSTKV LQAVQWLVSH 1570       1580       1590       1600       1610       1620
    CPHSLDLCCQ TLIQYVEDGI GHEFSGRFFH DRRERRLGGL ASQEPGAIIE LFNSVLQFLA 1630       1640       1650       1660       1670       1680
    SVVSSEQLCD LSWPVTEFAE AGGSRLLPHL HWNAPEHLAW LKQAVLGFQL PQMDLPPLGA 1690       1700       1710       1720       1730       1740
    PWLPVCSMVV QYASQIPSSR QTQPVLQSQV ENLLHRTYCR WKSKSPSPVH GAGPSVMEIP 1750       1760       1770       1780       1790       1800
    WDDLIALCIN HKLRDWTPPR LPVTSEALSE DGQICVYFFK NDLKKYDVPL SWEQARLQTQ 1810       1820       1830       1840       1850       1860
    KELQLREGRL AIKPFHPSAN NFPIPLLHMH RNWKRSTECA QEGRIPSTED LMRGASAEEL 1870       1880       1890       1900       1910       1920
    LAQCLSSSLL LEKEENKRFE DQLQQWLSED SGAFTDLTSL PLYLPQTLVS LSHTIEPVMK 1930       1940       1950       1960       1970       1980
    TSVTTSPQSD MMREQLQLSE ATGTCLGERL KHLERLIRSS REEEVASELH LSALLDMVDI
```

FIG.21B

SEQUENCE LISTING

```
<160> NUMBER OF SEQ ID NOS: 9

<210> SEQ ID NO 1
<211> LENGTH: 1971
<212> TYPE: PRT
<213> ORGANISM: Mouse

<400> SEQUENCE: 1

Met His Pro Val Asn Pro Phe Gly Gly Ser Ser Pro Ser Ala Phe Ala
1               5                   10                  15

Val Ser Ser Ser Thr Thr Gly Thr Tyr Gln Thr Lys Ser Pro Phe Arg
            20                  25                  30

Phe Gly Gln Pro Ser Leu Phe Gly Gln Asn Ser Thr Pro Ser Lys Ser
        35                  40                  45

Leu Ala Phe Ser Gln Val Pro Ser Phe Ala Thr Pro Ser Gly Gly Ser
    50                  55                  60

His Ser Ser Ser Leu Pro Ala Phe Gly Leu Thr Gln Thr Ser Ser Val
65                  70                  75                  80

Gly Leu Phe Ser Ser Leu Glu Ser Thr Pro Ser Phe Ala Ala Thr Ser
                85                  90                  95

Ser Ser Ser Val Pro Gly Asn Thr Ala Phe Ser Phe Lys Ser Thr Ser
            100                 105                 110

Ser Val Gly Val Phe Pro Ser Gly Ala Thr Phe Gly Pro Glu Thr Gly
        115                 120                 125

Glu Val Ala Gly Ser Gly Phe Arg Lys Thr Glu Phe Lys Phe Lys Pro
    130                 135                 140

Leu Glu Asn Ala Val Phe Lys Pro Ile Pro Gly Pro Glu Ser Glu Pro
145                 150                 155                 160

Glu Lys Thr Gln Ser Gln Ile Ser Ser Gly Phe Phe Thr Phe Ser His
                165                 170                 175
```

```
Pro Val Gly Ser Gly Ser Gly Gly Leu Thr Pro Phe Ser Phe Pro Gln
            180                 185                 190

Val Thr Asn Ser Ser Val Thr Ser Ser Ser Phe Ile Phe Ser Lys Pro
            195                 200                 205

Val Thr Ser Asn Thr Pro Ala Phe Ala Ser Pro Leu Ser Asn Gln Asn
            210                 215                 220

Val Glu Glu Lys Arg Val Ser Thr Ser Ala Phe Gly Ser Ser Asn
225                 230                 235                 240

Ser Ser Phe Ser Thr Phe Pro Thr Ala Ser Pro Gly Ser Leu Gly Glu
            245                 250                 255

Pro Phe Pro Ala Asn Lys Pro Ser Leu Arg Gln Gly Cys Glu Glu Ala
            260                 265                 270

Ile Ser Gln Val Glu Pro Leu Pro Thr Leu Met Lys Gly Leu Lys Arg
            275                 280                 285

Lys Glu Asp Gln Asp Arg Ser Pro Arg Arg His Cys His Glu Ala Ala
            290                 295                 300

Glu Asp Pro Asp Pro Leu Ser Arg Gly Asp His Pro Pro Asp Lys Arg
305                 310                 315                 320

Pro Val Arg Leu Asn Arg Pro Arg Gly Thr Leu Phe Gly Arg Thr
            325                 330                 335

Ile Gln Glu Val Phe Lys Ser Asn Lys Glu Ala Gly Arg Leu Gly Ser
            340                 345                 350

Lys Glu Ser Lys Glu Ser Gly Phe Ala Glu Pro Gly Glu Ser Asp His
            355                 360                 365

Ala Ala Val Pro Gly Gly Ser Gln Ser Thr Met Val Pro Ser Arg Leu
            370                 375                 380

Pro Ala Val Thr Lys Glu Glu Glu Ser Arg Asp Glu Lys Glu Asp
385                 390                 395                 400

Ser Leu Arg Gly Lys Ser Val Arg Gln Ser Lys Arg Glu Glu Trp
            405                 410                 415

Ile Tyr Ser Leu Gly Gly Val Ser Ser Leu Glu Leu Thr Ala Ile Gln
            420                 425                 430

Cys Lys Asn Ile Pro Asp Tyr Leu Asn Asp Arg Ala Ile Leu Glu Lys
            435                 440                 445

His Phe Ser Lys Ile Ala Lys Val Gln Arg Val Phe Thr Arg Arg Ser
            450                 455                 460

Lys Lys Leu Ala Val Ile His Phe Phe Asp His Ala Ser Ala Ala Leu
465                 470                 475                 480

Ala Arg Lys Lys Gly Lys Gly Leu His Lys Asp Val Val Ile Phe Trp
            485                 490                 495

His Lys Lys Lys Ile Ser Pro Ser Lys Lys Leu Phe Pro Leu Lys Glu
            500                 505                 510

Lys Leu Gly Glu Ser Glu Ala Ser Gln Gly Ile Glu Asp Ser Pro Phe
            515                 520                 525

Gln His Ser Pro Leu Ser Lys Pro Ile Val Arg Pro Ala Ala Gly Ser
            530                 535                 540

Leu Leu Ser Lys Ser Ser Pro Val Lys Lys Pro Ser Leu Leu Lys Met
545                 550                 555                 560

His Gln Phe Glu Ala Asp Pro Phe Asp Ser Gly Ser Glu Gly Ser Glu
            565                 570                 575

Gly Leu Gly Ser Cys Val Ser Ser Leu Ser Thr Leu Ile Gly Thr Val
            580                 585                 590

Ala Asp Thr Ser Glu Glu Lys Tyr Arg Leu Leu Asp Gln Arg Asp Arg
```

-continued

```
            595                 600                 605
Ile Met Arg Gln Ala Arg Val Lys Arg Thr Asp Leu Asp Lys Ala Arg
    610                 615                 620

Ala Phe Val Gly Thr Cys Pro Asp Met Cys Pro Glu Lys Glu Arg Tyr
625                 630                 635                 640

Leu Arg Glu Thr Arg Ser Gln Leu Ser Val Phe Glu Val Val Pro Gly
                645                 650                 655

Thr Asp Gln Val Asp His Ala Ala Val Lys Glu Tyr Ser Arg Ser
                660                 665                 670

Ser Ala Asp Gln Glu Glu Pro Leu Pro His Glu Leu Arg Pro Ser Ala
            675                 680                 685

Val Leu Ser Arg Thr Met Asp Tyr Leu Val Thr Gln Ile Met Asp Gln
    690                 695                 700

Lys Glu Gly Ser Leu Arg Asp Trp Tyr Asp Phe Val Trp Asn Arg Thr
705                 710                 715                 720

Arg Gly Ile Arg Lys Asp Ile Thr Gln Gln His Leu Cys Asp Pro Leu
                725                 730                 735

Thr Val Ser Leu Ile Glu Lys Cys Thr Arg Phe His Ile His Cys Ala
                740                 745                 750

His Phe Met Cys Glu Glu Pro Met Ser Ser Phe Asp Ala Lys Ile Asn
            755                 760                 765

Asn Glu Asn Met Thr Lys Cys Leu Gln Ser Leu Lys Glu Met Tyr Gln
    770                 775                 780

Asp Leu Arg Asn Lys Gly Val Phe Cys Ala Ser Glu Ala Glu Phe Gln
785                 790                 795                 800

Gly Tyr Asn Val Leu Leu Asn Leu Asn Lys Gly Asp Ile Leu Arg Glu
                805                 810                 815

Val Gln Gln Phe His Pro Asp Val Arg Asn Ser Pro Glu Val Asn Phe
                820                 825                 830

Ala Val Gln Ala Phe Ala Ala Leu Asn Ser Asn Asn Phe Val Arg Phe
            835                 840                 845

Phe Lys Leu Val Gln Ser Ala Ser Tyr Leu Asn Ala Cys Leu Leu His
    850                 855                 860

Cys Tyr Phe Asn Gln Ile Arg Lys Asp Ala Leu Arg Ala Leu Asn Val
865                 870                 875                 880

Ala Tyr Thr Val Ser Thr Gln Arg Ser Thr Val Phe Pro Leu Asp Gly
                885                 890                 895

Val Val Arg Met Leu Leu Phe Arg Asp Ser Glu Glu Ala Thr Asn Phe
                900                 905                 910

Leu Asn Tyr His Gly Leu Thr Val Ala Asp Gly Cys Val Glu Leu Asn
            915                 920                 925

Arg Ser Ala Phe Leu Glu Pro Glu Gly Leu Cys Lys Ala Arg Lys Ser
    930                 935                 940

Val Phe Ile Gly Arg Lys Leu Thr Val Ser Val Gly Glu Val Val Asn
945                 950                 955                 960

Gly Gly Pro Leu Pro Pro Val Pro Arg His Thr Pro Val Cys Ser Phe
                965                 970                 975

Asn Ser Gln Asn Lys Tyr Val Gly Glu Ser Leu Ala Thr Glu Leu Pro
            980                 985                 990

Ile Ser Thr Gln Arg Ala Gly Gly Asp Pro Ala Gly Gly Gly Arg Gly
            995                 1000                1005

Glu Asp Cys Glu Ala Glu Val  Asp Leu Pro Thr Leu  Ala Val Leu
    1010                1015                1020
```

-continued

```
Pro Gln Pro Pro Pro Ala Ser Ser Ala Thr Pro Ala Leu His Val
    1025                1030                1035
Gln Pro Leu Ala Pro Ala Ala Ala Pro Ser Leu Leu Gln Ala Ser
    1040                1045                1050
Thr Gln Pro Glu Val Leu Leu Pro Lys Pro Ala Pro Val Tyr Ser
    1055                1060                1065
Asp Ser Asp Leu Val Gln Val Val Asp Glu Leu Ile Gln Glu Ala
    1070                1075                1080
Leu Gln Val Asp Cys Glu Glu Val Ser Ser Ala Gly Ala Ala Tyr
    1085                1090                1095
Val Ala Ala Leu Gly Val Ser Asn Ala Ala Val Glu Asp Leu
    1100                1105                1110
Ile Thr Ala Ala Thr Thr Gly Ile Leu Arg His Val Ala Ala Glu
    1115                1120                1125
Glu Val Ser Met Glu Arg Gln Arg Leu Glu Glu Lys Gln Arg
    1130                1135                1140
Ala Glu Glu Glu Arg Leu Lys Gln Glu Arg Glu Leu Met Leu Thr
    1145                1150                1155
Gln Leu Ser Glu Gly Leu Ala Ala Glu Leu Thr Glu Leu Thr Val
    1160                1165                1170
Thr Glu Cys Val Trp Glu Thr Cys Ser Gln Glu Leu Gln Ser Ala
    1175                1180                1185
Val Lys Ile Asp Gln Lys Val Arg Val Ala Arg Cys Cys Glu Ala
    1190                1195                1200
Val Cys Ala His Leu Val Asp Leu Phe Leu Ala Glu Glu Ile Phe
    1205                1210                1215
Gln Thr Ala Lys Glu Thr Leu Gln Glu Leu Gln Cys Phe Cys Lys
    1220                1225                1230
Tyr Leu Gln Arg Trp Arg Glu Ala Val Ala Ala Arg Lys Lys Phe
    1235                1240                1245
Arg Arg Gln Met Arg Ala Phe Pro Ala Ala Pro Cys Cys Val Asp
    1250                1255                1260
Val Asn Asp Arg Leu Gln Ala Leu Val Pro Ser Ala Glu Cys Pro
    1265                1270                1275
Ile Thr Glu Glu Asn Leu Ala Lys Gly Leu Leu Asp Leu Gly His
    1280                1285                1290
Ala Gly Lys Val Gly Val Ser Cys Thr Arg Leu Arg Arg Leu Arg
    1295                1300                1305
Asn Lys Thr Ala His Gln Ile Lys Val Gln His Phe His Gln Gln
    1310                1315                1320
Leu Leu Arg Asn Ala Ala Trp Ala Pro Leu Asp Leu Pro Ser Ile
    1325                1330                1335
Val Ser Glu His Leu Pro Met Lys Gln Lys Arg Arg Phe Trp Lys
    1340                1345                1350
Leu Val Leu Val Leu Pro Asp Val Glu Glu Gln Thr Pro Glu Ser
    1355                1360                1365
Pro Gly Arg Ile Leu Glu Asn Trp Leu Lys Val Lys Phe Thr Gly
    1370                1375                1380
Asp Asp Ser Met Val Gly Asp Ile Gly Asp Asn Ala Gly Asp Ile
    1385                1390                1395
Gln Thr Leu Ser Val Phe Asn Thr Leu Ser Ser Lys Gly Asp Gln
    1400                1405                1410
```

```
Thr Val Ser Val Asn Val Cys Ile Lys Val Ala His Gly Thr Leu
    1415                1420                1425

Ser Asp Ser Ala Leu Asp Ala Val Glu Thr Gln Lys Asp Leu Leu
    1430                1435                1440

Gly Thr Ser Gly Leu Met Leu Leu Pro Pro Lys Val Lys Ser
    1445                1450                1455

Glu Glu Val Ala Glu Glu Leu Ser Trp Leu Ser Ala Leu Leu
    1460                1465                1470

Gln Leu Lys Gln Leu Leu Gln Ala Lys Pro Phe Gln Pro Ala Leu
    1475                1480                1485

Pro Leu Val Val Leu Val Pro Ser Ser Arg Gly Asp Ser Ala Gly
    1490                1495                1500

Arg Ala Val Glu Asp Gly Leu Met Leu Gln Asp Leu Val Ser Ala
    1505                1510                1515

Lys Leu Ile Ser Asp Tyr Ile Val Val Glu Ile Pro Asp Ser Val
    1520                1525                1530

Asn Asp Leu Gln Gly Thr Val Lys Val Ser Gly Ala Val Gln Trp
    1535                1540                1545

Leu Ile Ser Gly Cys Pro Gln Ala Leu Asp Leu Cys Cys Gln Thr
    1550                1555                1560

Leu Val Gln Tyr Val Glu Asp Gly Ile Ser Arg Glu Phe Ser Arg
    1565                1570                1575

Arg Phe Phe His Asp Arg Arg Glu Arg Arg Leu Ala Ser Leu Pro
    1580                1585                1590

Ser Gln Glu Pro Ser Thr Ile Ile Glu Leu Phe Asn Ser Val Leu
    1595                1600                1605

Gln Phe Leu Ala Ser Val Val Ser Ser Glu Gln Leu Cys Asp Ile
    1610                1615                1620

Ser Trp Pro Val Met Glu Phe Ala Glu Val Gly Gly Ser Gln Leu
    1625                1630                1635

Leu Pro His Leu His Trp Asn Ser Pro Glu His Leu Ala Trp Leu
    1640                1645                1650

Lys Gln Ala Val Leu Gly Phe Gln Leu Pro Gln Met Asp Leu Pro
    1655                1660                1665

Pro Pro Gly Ala Pro Trp Leu Pro Val Cys Ser Met Val Ile Gln
    1670                1675                1680

Tyr Thr Ser Gln Ile Pro Ser Ser Ser Gln Thr Gln Pro Val Leu
    1685                1690                1695

Gln Ser Gln Ala Glu Asn Leu Leu Cys Arg Thr Tyr Gln Lys Trp
    1700                1705                1710

Lys Asn Lys Ser Leu Ser Pro Gly Gln Glu Leu Gly Pro Ser Val
    1715                1720                1725

Ala Glu Ile Pro Trp Asp Asp Ile Ile Thr Leu Cys Ile Asn His
    1730                1735                1740

Lys Leu Arg Asp Trp Thr Pro Pro Arg Leu Pro Val Thr Leu Glu
    1745                1750                1755

Ala Leu Ser Glu Asp Gly Gln Ile Cys Val Tyr Phe Phe Lys Asn
    1760                1765                1770

Leu Leu Arg Lys Tyr His Val Pro Ser Ser Trp Glu Gln Ala Arg
    1775                1780                1785

Met Gln Thr Gln Arg Glu Leu Gln Leu Ser His Gly Arg Ser Gly
    1790                1795                1800

Met Arg Ser Ile His Pro Pro Thr Ser Thr Phe Pro Thr Pro Leu
```

-continued

| | | 1805 | | | 1810 | | | | 1815 | | |
|---|---|---|---|---|---|---|---|---|---|---|---|
| Leu | His | Val | His | Gln | Lys | Gly | Lys | Lys | Glu | Glu | Ser | Gly | Arg |
| 1820 | | | | 1825 | | | | 1830 | | | |

| Glu | Gly | Ser | Leu | Ser | Thr | Glu | Asp | Leu | Leu | Arg | Gly | Ala | Ser | Ala |
| 1835 | | | | | 1840 | | | | | 1845 | | |

Glu Gly Ser Leu Ser Thr Glu Asp Leu Leu Arg Gly Ala Ser Ala
     1835                1840                1845

Glu Glu Leu Leu Ala Gln Ser Leu Ser Ser Ser Leu Leu Glu Glu
     1850                1855                1860

Lys Glu Glu Asn Lys Arg Phe Glu Asp Gln Leu Gln Gln Trp Leu
     1865                1870                1875

Ser Gln Asp Ser Gln Ala Phe Thr Glu Ser Thr Arg Leu Pro Leu
     1880                1885                1890

Tyr Leu Pro Gln Thr Leu Val Ser Phe Pro Asp Ser Ile Lys Thr
     1895                1900                1905

Gln Thr Met Val Lys Thr Ser Thr Ser Pro Gln Asn Ser Gly Thr
     1910                1915                1920

Gly Lys Gln Leu Arg Phe Ser Glu Ala Ser Gly Ser Ser Leu Thr
     1925                1930                1935

Glu Lys Leu Lys Leu Leu Glu Arg Leu Ile Gln Ser Ser Arg Ala
     1940                1945                1950

Glu Glu Ala Ala Ser Glu Leu His Leu Ser Ala Leu Leu Glu Met
     1955                1960                1965

Val Asp Met
     1970

<210> SEQ ID NO 2
<211> LENGTH: 6429
<212> TYPE: DNA
<213> ORGANISM: Mouse

<400> SEQUENCE: 2

```
gttgcggtgc ggtgggcccg gtagaggctg cacgcagact gtgggcgagc acaagcgctg     60
gcgacagtgg ccgtatctgg cggacttgct cctccctccg cggcctccgc tgtcccttgt    120
gtctttgccg agttgctgaa ggccttcact agtcttcgct cgaaggcgtc tgttaaccta    180
gcggccggct tccggagtgt taagcatcgg ggataaaaag ctattatttc tagaccaggg    240
catcgcaagt tcgagttacc gggagaaaaa tgagatggtc atcctgagga tgaaggagag    300
cttcccctgg caacagataa tttaaagagg agagctactt gtgtatagtc catatttatt    360
gccttcagat aattggcttg aagatgcacc cggtgaaccc cttcggaggc agcagcccaa    420
gtgcttttgc ggtatcttcc agcaccacgg gaacatatca gactaaatca ccatttcgat    480
ttggccagcc ttccctttt ggacagaaca gcacacccag caagagcctg gcgttttcac     540
aagtaccaag ctttgcaaca ccctctggag gaagccattc ttcctccttg ccagcatttg    600
gactcaccca aacctcaagt gtgggactct tctctagtct cgaatccaca ccttctttcg    660
cagctacttc gagttcctct gtgcccggca atacggcatt cagctttaag tcaacctcta    720
gcgttggggt tttcccaagt ggcgctactt ttgggccaga aaccggagaa gtagcaggtt    780
ctggctttcg gaagacggaa ttcaagttta aacctctgga aaatgcagtc ttcaaaccga    840
taccgggggcc tgagtcagag ccagaaaaaa cccagagcca gatttcttct ggatttttta    900
cattttccca tcccgttggt agcgggtctg gaggcctgac ccctttttct ttcccacagg    960
tgacaaaatag ttcggtgact agctcaagtt ttatctttc gaaaccagtt actagtaata   1020
ctcctgcctt tgcctctcct tgtctaacc aaaatgtaga agaagagaag agggtttcta   1080
```

```
cgtcagcgtt tggaagctca aacagtagct tcagtacttt ccccacacgcg tcaccaggat    1140
ctttggggga gcccttccca gctaacaaac caagcctccg ccaaggatgt gaggaagcca    1200
tctcccaggt ggagccactt cccaccctca tgaagggatt aaagaggaaa gaggaccagg    1260
atcgctcccc gaggagacat tgccacgagg cagcagaaga ccctgatccc ctgtccaggg    1320
gcgaccatcc cccagataaa cggccagtcc gcctcaacag accccgggga ggtactttgt    1380
ttggccggac aatacaggag gtcttcaaaa gcaataaaga ggcaggccgc ctgggcagca    1440
aggaatccaa ggagagtggc tttgcggaac tggggaaag tgaccacgcg gccgtcccag    1500
gagggagtca gtccaccatg gtaccttccc gccttccagc tgtgactaaa gaggaagaag    1560
aaagtagaga tgagaaagaa gattctctca ggggaaagtc tgtgcgccag agtaagcgaa    1620
gggaagagtg gatctacagc ctcggggcg tgtcttcttt agagctcaca gccatccagt    1680
gcaagaacat ccccgactac ctcaacgaca gagccatcct ggagaaacac ttcagcaaaa    1740
tcgctaaagt ccagcgggtc ttcaccagac gcagcaagaa gctcgccgtg attcattttt    1800
tcgaccacgc atcggcagcc ctggctagga gaaggggaa aggtctgcat aaggacgtgg    1860
ttatcttttg gcacaagaag aaaataagtc ccagcaagaa actctttccc ctgaaggaga    1920
agcttggtga gagtgaagcc agccagggca tcgaggactc ccctttcag cactcgcctc    1980
tcagcaagcc catcgtgagg cctgcagccg gcagcctcct cagcaaaagc tctccagtga    2040
agaagccgag tcttctgaag atgcaccagt ttgaggcgga tccttttgac tctggatctg    2100
agggctccga gggccttggt tcttgcgtgt catctcttag caccctgata gggactgtgg    2160
cagacacatc tgaggagaag taccgccttc tggaccagag agaccgcatc atgcggcaag    2220
ctcgagtgaa gaggacggac ctggacaaag ccagggcatt tgttgggact tgccctgaca    2280
tgtgtcccga gaaggagcgg tacttgaggg agacccggag ccagctgagc gtgtttgaag    2340
ttgtcccagg gactgaccag gtggaccatg cagcagccgt gaaggagtac agccggtcct    2400
ctgcagatca ggaggagccc ctgccacatg agctgagacc ctcagcagtt ctcagcagga    2460
ccatggacta cctggtgacc cagatcatgg accaaaagga aggcagcctt cgggattggt    2520
atgacttcgt gtggaaccgc acccggggta tacgaaagga cataacacag cagcacctct    2580
gtgatcccct gacggtgtct ctgatcgaga agtgtacccg atttcacatt cactgtgccc    2640
actttatgtg tgaggagcct atgtcttcct ttgatgccaa gatcaacaat gagaacatga    2700
ccaagtgtct acagagtctg aaggagatgt accaggacct gaggaacaag ggtgtttttt    2760
gtgccagtga agcagagttt cagggctaca atgtcctgct taatctcaac aaaggagaca    2820
ttttgagaga agtgcagcag ttccaccctg acgttaggaa ctccccagag gtgaacttcg    2880
ctgtccaggc ttttgctgca ttgaacagca ataattttgt gagatttttc aaactggttc    2940
agtcagcttc ttacctgaat gcgtgcctgt tacactgtta cttttaatcag atccgcaagg    3000
atgccctccg ggcactcaat gttgcttata ctgtaagcac acagcgctct accgtcttcc    3060
ccctggatgg tgtcgtccgc atgctgctgt tcagagatag tgaagaggcg acaaacttcc    3120
tcaattacca tggcctcact gtagctgatg ctgtgttga gctgaatcgg tcggcattct    3180
tggaaccgga gggattatgc aaggccagga agtcagtgtt tattggccgg aagctgacgg    3240
tgtcagttgg ggaagttgtg aatggagggc cgttgccccc tgttcctcgc catacacctg    3300
tgtgcagctt caactcccag aataagtacg ttggagagag cctggctacg gagctgccca    3360
tcagcactca gagagctggt ggagacccag caggtggtgg cagaggagag gactgtgagg    3420
cagaggtgga cttgccaaca ttggcggtcc tcccacagcc gcctcctgca tcctcagcca    3480
```

```
cgccggcgct tcatgtccag ccactggccc cagccgcagc acccagcctt ctccaggcct    3540
ccacgcagcc tgaggtgctg cttccaaagc ctgcgcctgt gtactctgac tcggacctgg    3600
tacaggtggt ggacgagctc atccaggagg ctctgcaagt ggactgtgag gaagtcagct    3660 ccgctgggc agcctacgta gccgcagctc tgggcgtttc caatgctgct gtggaggatc    3720
tgattactgc tgcgaccacg ggcattctga ggcacgttgc cgctgaggaa gtttccatgg    3780
aaaggcagag actagaggaa gagaagcaac gagctgagga ggaacggttg aagcaagaga    3840
gagaactgat gttaactcag ctgagcgagg gtctggccgc agagctgaca gaactcacgg    3900
tgacagagtg tgtgtgggaa acctgctctc aggagctaca gagtgcagta aaaatagacc    3960
agaaggtccg tgtggcccgc tgttgtgaag ccgtctgtgc acacctggtg gatttgtttc    4020
ttgctgagga aattttccag actgcaaaag agacactcca ggaactccag tgtttctgca    4080
agtatctaca acgtggagg gaggctgttg cagctcggaa gaaattccgg cgtcagatgc    4140
gggccttccc tgcagcgcca tgctgtgtgg atgtgaatga ccggctgcag gcactagtgc    4200
ccagcgcaga gtgccccatt actgaggaga acctggccaa gggtcttttg gacctgggcc    4260
acgcaggcaa agtaggcgtc tcctgtacca ggttgaggcg gcttagaaac aagacagctc    4320
accagataaa ggtccagcac ttccaccagc agctgctgag gaatgctgca tgggcacctc    4380
tggacctgcc atccattgtg tctgagcacc tccccatgaa gcagaagcga aggttttgga    4440
aactggtgct ggtgttgcct gatgtggaag agcagactcc agagagtcct ggcagaatac    4500
tagaaaactg gctaaaggtc aaattcacag gagatgacag catggtgggt gacataggag    4560
ataatgctgg tgatatccag accctctcag tctttaatac acttagtagt aaaggggatc    4620
aaacagtttc tgtcaacgtg tgtataaagg tggctcatgg caccttagt gacagtgccc    4680 ttgatgctgt ggagacccag aaggacctgt tgggaaccag tgggctcatg ctgctgcttc    4740
ccccgaaagt gaagagtgag gaggtggcag aggaggaact gtcctggctg tcggctttac    4800
tgcagctcaa gcagcttctg caggccaagc ccttccagcc tgcctgccg ctggtggtcc    4860 tcgtgcccag ctccagaggg gactccgcgg ggagggcagt agaggacggt ctgatgttac    4920
aggatttggt ttcagccaag ctgatttccg attacattgt tgttgagatt cctgactctg    4980
ttaatgattt acaaggcaca gtgaaggttt ctggagcagt ccagtggctg atctccggat    5040
gtcctcaagc cctagacctt tgctgccaga cccttgttca gtatgttgag gatgggatca    5100
gccgcgagtt cagccgtcgg ttttttccacg acaggagaga gaggcgcctg gctagcctgc    5160
cctcccagga gcctagcacc attattgagt tgttcaacag tgtgctgcag ttcctggcct    5220
ctgtggtatc ctctgagcag ctgtgtgaca tctcctggcc tgtcatggaa tttgccgaag    5280
tgggaggcag ccagctgctt cctcacctgc actggaactc accagagcat ctagcgtggc    5340
tgaaacaagc tgtgcttggg ttccagcttc cacagatgga ccttccaccc caggggccc    5400 cctggctccc tgtgtgttcc atggtcattc agtacacctc ccagattccc agctcaagcc    5460
agacacagcc tgtcctccag tcccaggcgg agaacctgct gtgcagaaca taccagaagt    5520
ggaagaacaa gagcctctct ccaggccagg agttggggcc ttctgttgcc gagatcccgt    5580
gggatgacat catcacctta tgcatcaatc ataagctgag ggactggaca ccccccaggc    5640
tccctgtcac attagaggcg ctgagtgaag atggtcaaat atgtgtgtat ttttcaaaa    5700 acctttaag aaaataccac gttccctcgt catgggaaca ggccagaatg cagacgcagc    5760
gggaactgca gctgagtcat ggacgttcgg ggatgaggtc catccatcct cctacaagca    5820
```

-continued

```
cttttcctac tccattgctt catgtacacc agaaagggaa gaaaaaggaa gagagtggcc    5880
gagaggggag cctcagtaca gaggacctcc tgcgggggc ttctgcagaa gagctcctgg     5940
cacagagtct gtccagcagt cttctggaag agaaggaaga gaacaagagg tttgaagatc    6000
aacttcagca gtggttatcg caagactcac aggcattcac agagtcaact cggcttcctc    6060
tctacctccc tcagacgcta gtgtcctttc ctgattctat caaaactcag accatggtga    6120
aaacatctac aagtcctcag aattcaggaa caggaaagca gttgaggttc tcagaggcat    6180
ccggttcatc cctgacggaa aagctgaagc tcctggaaag gctgatccag agctcaaggg    6240
cggaagaagc agcctccgag ctgcacctct ctgcactgct ggagatggtg acatgtagc    6300 tgtctgacgg gagacggatc tctaattcat aatgctttgt ctgtattcaa ttgtgttata    6360
gatgctgttg gaaatgtgac tattaattat gcaaataaac ttttttgaatc attccaaaaa    6420 aaaaaccat                                                              6429
```

<210> SEQ ID NO 3
<211> LENGTH: 1980
<212> TYPE: PRT
<213> ORGANISM: Homo sapiens

<400> SEQUENCE: 3

```
Met Asn Pro Thr Asn Pro Phe Ser Gly Gln Gln Pro Ser Ala Phe Ser
1               5                   10                  15

Ala Ser Ser Ser Asn Val Gly Thr Leu Pro Ser Lys Pro Pro Phe Arg
            20                  25                  30

Phe Gly Gln Pro Ser Leu Phe Gly Gln Asn Ser Thr Leu Ser Gly Lys
        35                  40                  45

Ser Ser Gly Phe Ser Gln Val Ser Ser Phe Pro Ala Ser Ser Gly Val
    50                  55                  60

Ser His Ser Ser Val Gln Thr Leu Gly Phe Thr Gln Thr Ser Ser
65                  70                  75                  80

Val Gly Pro Phe Ser Gly Leu Glu His Thr Ser Thr Phe Val Ala Thr
                85                  90                  95

Ser Gly Pro Ser Ser Ser Val Leu Gly Asn Thr Gly Phe Ser Phe
            100                 105                 110

Lys Ser Pro Thr Ser Val Gly Ala Phe Pro Ser Thr Ser Ala Phe Gly
        115                 120                 125

Gln Glu Ala Gly Glu Ile Val Asn Ser Gly Phe Gly Lys Thr Glu Phe
    130                 135                 140

Ser Phe Lys Pro Leu Glu Asn Ala Val Phe Lys Pro Ile Leu Gly Ala
145                 150                 155                 160

Glu Ser Glu Pro Glu Lys Thr Gln Ser Gln Ile Ala Ser Gly Phe
                165                 170                 175

Thr Phe Ser His Pro Ile Ser Ser Ala Pro Gly Gly Leu Ala Pro Phe
            180                 185                 190

Ser Phe Pro Gln Val Thr Ser Ser Ala Thr Thr Ser Asn Phe Thr
        195                 200                 205

Phe Ser Lys Pro Val Ser Ser Asn Ser Leu Ser Ala Phe Thr Pro
    210                 215                 220

Ala Leu Ser Asn Gln Asn Val Glu Glu Lys Arg Gly Pro Lys Ser
225                 230                 235                 240

Ile Phe Gly Ser Ser Asn Asn Ser Phe Ser Phe Pro Val Ser Ser
                245                 250                 255

Ala Val Leu Gly Glu Pro Phe Gln Ala Ser Lys Ala Gly Val Arg Gln
```

-continued

```
                260                 265                 270
Gly Cys Glu Ala Val Ser Gln Val Glu Pro Leu Pro Ser Leu Met
            275                 280                 285
Lys Gly Leu Lys Arg Lys Glu Asp Gln Asp Arg Ser Pro Arg His
        290                 295                 300
Gly His Glu Pro Ala Glu Asp Ser Asp Pro Leu Ser Arg Gly Asp His
305                 310                 315                 320
Pro Pro Asp Lys Arg Pro Val Arg Leu Asn Arg Pro Arg Gly Gly Thr
                325                 330                 335
Leu Phe Gly Arg Thr Ile Gln Asp Val Phe Lys Ser Asn Lys Glu Val
            340                 345                 350
Gly Arg Leu Gly Asn Lys Glu Ala Lys Lys Glu Thr Gly Phe Val Glu
        355                 360                 365
Ser Ala Glu Ser Asp His Met Ala Ile Pro Gly Gly Asn Gln Ser Val
        370                 375                 380
Leu Ala Pro Ser Arg Ile Pro Gly Val Asn Lys Glu Glu Thr Glu
385                 390                 395                 400
Ser Arg Glu Lys Lys Glu Asp Ser Leu Arg Gly Thr Pro Ala Arg Gln
                405                 410                 415
Ser Asn Arg Ser Glu Ser Thr Asp Ser Leu Gly Gly Leu Ser Pro Ser
                420                 425                 430
Glu Val Thr Ala Ile Gln Cys Lys Asn Ile Pro Asp Tyr Leu Asn Asp
            435                 440                 445
Arg Thr Ile Leu Glu Asn His Phe Gly Lys Ile Ala Lys Val Gln Arg
        450                 455                 460
Ile Phe Thr Arg Arg Ser Lys Lys Leu Ala Val Val His Phe Asp
465                 470                 475                 480
His Ala Ser Ala Ala Leu Ala Arg Lys Lys Gly Lys Ser Leu His Lys
                485                 490                 495
Asp Met Ala Ile Phe Trp His Arg Lys Lys Ile Ser Pro Asn Lys Lys
                500                 505                 510
Pro Phe Ser Leu Lys Glu Lys Lys Pro Gly Asp Gly Glu Val Ser Pro
            515                 520                 525
Ser Thr Glu Asp Ala Pro Phe Gln His Ser Pro Leu Gly Lys Ala Ala
        530                 535                 540
Gly Arg Thr Gly Ala Ser Ser Leu Leu Asn Lys Ser Ser Pro Val Lys
545                 550                 555                 560
Lys Pro Ser Leu Leu Lys Ala His Gln Phe Glu Gly Asp Ser Phe Asp
            565                 570                 575
Ser Ala Ser Glu Gly Ser Glu Gly Leu Gly Pro Cys Val Leu Ser Leu
        580                 585                 590
Ser Thr Leu Ile Gly Thr Val Ala Glu Thr Ser Lys Glu Lys Tyr Arg
        595                 600                 605
Leu Leu Asp Gln Arg Asp Arg Ile Met Arg Gln Ala Arg Val Lys Arg
        610                 615                 620
Thr Asp Leu Asp Lys Ala Arg Thr Phe Val Gly Thr Cys Leu Asp Met
625                 630                 635                 640
Cys Pro Glu Lys Glu Arg Tyr Met Arg Glu Thr Arg Ser Gln Leu Ser
                645                 650                 655
Val Phe Glu Val Val Pro Gly Thr Asp Gln Val Asp His Ala Ala Ala
            660                 665                 670
Val Lys Glu Tyr Ser Arg Ser Ser Ala Asp Gln Glu Glu Pro Leu Pro
        675                 680                 685
```

```
His Glu Leu Arg Pro Leu Pro Val Leu Ser Arg Thr Met Asp Tyr Leu
    690                 695                 700
Val Thr Gln Ile Met Asp Gln Lys Glu Gly Ser Leu Arg Asp Trp Tyr
705                 710                 715                 720
Asp Phe Val Trp Asn Arg Thr Arg Gly Ile Arg Lys Asp Ile Thr Gln
                725                 730                 735
Gln His Leu Cys Asp Pro Leu Thr Val Ser Leu Ile Glu Lys Cys Thr
                740                 745                 750
Arg Phe His Ile His Cys Ala His Phe Met Cys Glu Glu Pro Met Ser
                755                 760                 765
Ser Phe Asp Ala Lys Ile Asn Asn Glu Asn Met Thr Lys Cys Leu Gln
770                 775                 780
Ser Leu Lys Glu Met Tyr Gln Asp Leu Arg Asn Lys Gly Val Phe Cys
785                 790                 795                 800
Ala Ser Glu Ala Glu Phe Gln Gly Tyr Asn Val Leu Leu Ser Leu Asn
                805                 810                 815
Lys Gly Asp Ile Leu Arg Glu Val Gln Gln Phe His Pro Ala Val Arg
                820                 825                 830
Asn Ser Ser Glu Val Lys Phe Ala Val Gln Ala Phe Ala Ala Leu Asn
                835                 840                 845
Ser Asn Asn Phe Val Arg Phe Phe Lys Leu Val Gln Ser Ala Ser Tyr
850                 855                 860
Leu Asn Ala Cys Leu Leu His Cys Tyr Phe Ser Gln Ile Arg Lys Asp
865                 870                 875                 880
Ala Leu Arg Ala Leu Asn Phe Ala Tyr Thr Val Ser Thr Gln Arg Ser
                885                 890                 895
Thr Ile Phe Pro Leu Asp Gly Val Val Arg Met Leu Leu Phe Arg Asp
                900                 905                 910
Cys Glu Glu Ala Thr Asp Phe Leu Thr Cys His Gly Leu Thr Val Ser
                915                 920                 925
Asp Gly Cys Val Glu Leu Asn Arg Ser Ala Phe Leu Glu Pro Glu Gly
    930                 935                 940
Leu Ser Lys Thr Arg Lys Ser Val Phe Ile Thr Arg Lys Leu Thr Val
945                 950                 955                 960
Ser Val Gly Glu Ile Val Asn Gly Gly Pro Leu Pro Val Pro Arg
                965                 970                 975
His Thr Pro Val Cys Ser Phe Asn Ser Gln Asn Lys Tyr Ile Gly Glu
                980                 985                 990
Ser Leu Ala Ala Glu Leu Pro Val Ser Thr Gln Arg Pro Gly Ser Asp
    995                 1000                1005
Thr Val Gly Gly Gly Arg Gly Glu Glu Cys Gly Val Glu Pro Asp
    1010                1015                1020
Ala Pro Leu Ser Ser Leu Pro Gln Ser Leu Pro Ala Pro Ala Pro
    1025                1030                1035
Ser Pro Val Pro Leu Pro Pro Val Leu Ala Leu Thr Pro Ser Val
    1040                1045                1050
Ala Pro Ser Leu Phe Gln Leu Ser Val Gln Pro Glu Pro Pro Pro
    1055                1060                1065
Pro Glu Pro Val Pro Met Tyr Ser Asp Glu Asp Leu Ala Gln Val
    1070                1075                1080
Val Asp Glu Leu Ile Gln Glu Ala Leu Gln Arg Asp Cys Glu Glu
    1085                1090                1095
```

```
Val Gly Ser Ala Gly Ala Ala Tyr Ala Ala Ala Leu Gly Val
    1100            1105            1110

Ser Asn Ala Ala Met Glu Asp Leu Leu Thr Ala Ala Thr Thr Gly
    1115            1120            1125

Ile Leu Arg His Ile Ala Ala Glu Glu Val Ser Lys Glu Arg Glu
    1130            1135            1140

Arg Arg Glu Gln Glu Arg Gln Arg Ala Glu Glu Arg Leu Lys
    1145            1150            1155

Gln Glu Arg Glu Leu Val Leu Ser Glu Leu Ser Gln Gly Leu Ala
    1160            1165            1170

Val Glu Leu Met Glu Arg Val Met Met Glu Phe Val Arg Glu Thr
    1175            1180            1185

Cys Ser Gln Glu Leu Lys Asn Ala Val Glu Thr Asp Gln Arg Val
    1190            1195            1200

Arg Val Ala Arg Cys Cys Glu Asp Val Cys Ala His Leu Val Asp
    1205            1210            1215

Leu Phe Leu Val Glu Glu Ile Phe Gln Thr Ala Lys Glu Thr Leu
    1220            1225            1230

Gln Glu Leu Gln Cys Phe Cys Lys Tyr Leu Gln Arg Trp Arg Glu
    1235            1240            1245

Ala Val Thr Ala Arg Lys Lys Leu Arg Arg Gln Met Arg Ala Phe
    1250            1255            1260

Pro Ala Ala Pro Cys Cys Val Asp Val Ser Asp Arg Leu Arg Ala
    1265            1270            1275

Leu Ala Pro Ser Ala Glu Cys Pro Ile Ala Glu Asn Leu Ala
    1280            1285            1290

Arg Gly Leu Leu Asp Leu Gly His Ala Gly Arg Leu Gly Ile Ser
    1295            1300            1305

Cys Thr Arg Leu Arg Arg Leu Arg Asn Lys Thr Ala His Gln Met
    1310            1315            1320

Lys Val Gln His Phe Tyr Gln Gln Leu Leu Ser Asp Val Ala Trp
    1325            1330            1335

Ala Ser Leu Asp Leu Pro Ser Leu Val Ala Glu His Leu Pro Gly
    1340            1345            1350

Arg Gln Glu His Val Phe Trp Lys Leu Val Leu Val Leu Pro Asp
    1355            1360            1365

Val Glu Glu Gln Ser Pro Glu Ser Cys Gly Arg Ile Leu Ala Asn
    1370            1375            1380

Trp Leu Lys Val Lys Phe Met Gly Asp Glu Gly Ser Val Asp Asp
    1385            1390            1395

Thr Ser Ser Asp Ala Gly Gly Ile Gln Thr Leu Ser Leu Phe Asn
    1400            1405            1410

Ser Leu Ser Ser Lys Gly Asp Gln Met Ile Ser Val Asn Val Cys
    1415            1420            1425

Ile Lys Val Ala His Gly Ala Leu Ser Asp Gly Ala Ile Asp Ala
    1430            1435            1440

Val Glu Thr Gln Lys Asp Leu Leu Gly Ala Ser Gly Leu Met Leu
    1445            1450            1455

Leu Leu Pro Pro Lys Met Lys Ser Glu Asp Met Ala Glu Glu Asp
    1460            1465            1470

Val Tyr Trp Leu Ser Ala Leu Leu Gln Leu Lys Gln Leu Leu Gln
    1475            1480            1485

Ala Lys Pro Phe Gln Pro Ala Leu Pro Leu Val Val Leu Val Pro
```

-continued

```
                1490                1495                1500

Ser Pro Gly Gly Asp Ala Val Glu Lys Glu Val Glu Asp Gly Leu
           1505                1510                1515

Met Leu Gln Asp Leu Val Ser Ala Lys Leu Ile Ser Asp Tyr Thr
           1520                1525                1530

Val Thr Glu Ile Pro Asp Thr Ile Asn Asp Leu Gln Gly Ser Thr
           1535                1540                1545

Lys Val Leu Gln Ala Val Gln Trp Leu Val Ser His Cys Pro His
           1550                1555                1560

Ser Leu Asp Leu Cys Cys Gln Thr Leu Ile Gln Tyr Val Glu Asp
           1565                1570                1575

Gly Ile Gly His Glu Phe Ser Gly Arg Phe Phe His Asp Arg Arg
           1580                1585                1590

Glu Arg Arg Leu Gly Gly Leu Ala Ser Gln Glu Pro Gly Ala Ile
           1595                1600                1605

Ile Glu Leu Phe Asn Ser Val Leu Gln Phe Leu Ala Ser Val Val
           1610                1615                1620

Ser Ser Glu Gln Leu Cys Asp Leu Ser Trp Pro Val Thr Glu Phe
           1625                1630                1635

Ala Glu Ala Gly Gly Ser Arg Leu Leu Pro His Leu His Trp Asn
           1640                1645                1650

Ala Pro Glu His Leu Ala Trp Leu Lys Gln Ala Val Leu Gly Phe
           1655                1660                1665

Gln Leu Pro Gln Met Asp Leu Pro Pro Leu Gly Ala Pro Trp Leu
           1670                1675                1680

Pro Val Cys Ser Met Val Val Gln Tyr Ala Ser Gln Ile Pro Ser
           1685                1690                1695

Ser Arg Gln Thr Gln Pro Val Leu Gln Ser Gln Val Glu Asn Leu
           1700                1705                1710

Leu His Arg Thr Tyr Cys Arg Trp Lys Ser Lys Ser Pro Ser Pro
           1715                1720                1725

Val His Gly Ala Gly Pro Ser Val Met Glu Ile Pro Trp Asp Asp
           1730                1735                1740

Leu Ile Ala Leu Cys Ile Asn His Lys Leu Arg Asp Trp Thr Pro
           1745                1750                1755

Pro Arg Leu Pro Val Thr Ser Glu Ala Leu Ser Glu Asp Gly Gln
           1760                1765                1770

Ile Cys Val Tyr Phe Phe Lys Asn Asp Leu Lys Lys Tyr Asp Val
           1775                1780                1785

Pro Leu Ser Trp Glu Gln Ala Arg Leu Gln Thr Gln Lys Glu Leu
           1790                1795                1800

Gln Leu Arg Glu Gly Arg Leu Ala Ile Lys Pro Phe His Pro Ser
           1805                1810                1815

Ala Asn Asn Phe Pro Ile Pro Leu Leu His Met His Arg Asn Trp
           1820                1825                1830

Lys Arg Ser Thr Glu Cys Ala Gln Glu Gly Arg Ile Pro Ser Thr
           1835                1840                1845

Glu Asp Leu Met Arg Gly Ala Ser Ala Glu Glu Leu Leu Ala Gln
           1850                1855                1860

Cys Leu Ser Ser Ser Leu Leu Leu Glu Lys Glu Glu Asn Lys Arg
           1865                1870                1875

Phe Glu Asp Gln Leu Gln Gln Trp Leu Ser Glu Asp Ser Gly Ala
           1880                1885                1890
```

-continued

```
Phe Thr Asp Leu Thr Ser Leu Pro Leu Tyr Leu Pro Gln Thr Leu
    1895                1900                1905
Val Ser Leu Ser His Thr Ile Glu Pro Val Met Lys Thr Ser Val
1910                1915                1920
Thr Thr Ser Pro Gln Ser Asp Met Met Arg Glu Gln Leu Gln Leu
1925                1930                1935
Ser Glu Ala Thr Gly Thr Cys Leu Gly Glu Arg Leu Lys His Leu
1940                1945                1950
Glu Arg Leu Ile Arg Ser Ser Arg Glu Glu Glu Val Ala Ser Glu
    1955                1960                1965
Leu His Leu Ser Ala Leu Leu Asp Met Val Asp Ile
1970                1975                1980

<210> SEQ ID NO 4
<211> LENGTH: 6114
<212> TYPE: DNA
<213> ORGANISM: Homo sapiens

<400> SEQUENCE: 4
gtaatactta attaccttct aataattgga gcagaagatg aacccaacta atcctttcag      60
tgggcagcag cctagtgctt tttcggcgtc ttctagtaat gtaggaacac ttccatctaa     120
gccgccattt cgatttggtc aaccttctct ttttggacaa acagtacct tatctgggaa      180
gagctcggga ttttcacagg tatccagctt ccagcgtct tctggagtaa gtcattcctc     240
ttcagtgcaa acattagggt tcacccaaac ctcaagtgtt ggacccttt ctggacttga     300
gcacacttcc acctttgtgg ctacctctgg ccttcaagt tcatctgtgc tgggaaacac     360
aggatttagt tttaaatcac ccaccagtgt tgggcttt ccaagcactt ctgcttttgg     420
acaagaagct ggagaaatag tgaactctgg ttttgggaaa acagaattca gctttaaacc     480
tctggaaaat gcagtgttca aaccaatact gggggctgaa tctgagccag agaaaaccca    540
gagccaaatt gcttctgggt tttttacatt ttccacccca attagtagtg cacctggagg    600
cctggcccct ttctcttttc ctcaagtaac aagtagttca gctaccactt caaattttac    660
cttttcaaaa cctgttagta gtaataattc attatctgcc tttaccctg ctttgtcaaa    720
ccaaaatgta gaggaagaga agagaggacc taagtcaata tttggaagtt ctaataatag    780
cttcagtagc ttccctgtat catctgcggt tttgggcgaa cctttccagg ctagcaaagc   840
aggtgtcagg caggggtgtg aagaagctgt tcccaggtg gaaccacttc ccagcctaat    900
gaaaggactg aaaaggaagg aggaccagga tcgctcccca aggagacatg gccacgagcc    960
agcagaagat tcggatcctc tgtcccgggg cgatcatcct ccagacaaac gacctgtccg   1020
cctgaatcga ccccggggag gtactttatt tggtcggacg atacaggatg ttttcaaaag   1080
caataaggaa gtaggtcgtc tgggcaacaa ggaggccaaa aaggaaactg ctttgttga   1140
gtctgcagaa agtgaccaca tggctatccc aggagggaat cagtctgtcc tggcacttc   1200
ccggattcca ggtgtgaata agaggaaga aactgaaagt agagagaaga aagaagattc   1260
tctaagagga actccggcgc gtcagagtaa cagaagcgag agcacagaca gtcttggggg   1320
cttgtctccc tctgaagtca cagccatcca gtgcaagaac atccctgact acctcaacga   1380
caggaccatt ctggagaacc attttggcaa aattgctaaa gtgcagcgca tctttaccag   1440
gcgcagcaaa aagcttgcag tggtacattt ctttgatcat gcatctgcag ccctggctag   1500
aaagaagggg aaaagtttgc ataaagacat ggctatcttt tggcacagga agaaaataag   1560
```

-continued

```
ccccaataag aaacccttttt ccctgaagga gaagaaacca ggtgacggtg aagtcagccc    1620
gagcacagag gatgcaccct ttcagcactc tcctcttggc aaggccgcag ggaggactgg    1680
tgctagcagc ctcctgaata aaagctctcc agtgaagaag ccaagtcttc taaaggccca    1740
ccaattcgag ggagactctt ttgactcagc ctccgagggc tccgagggcc tcggccatg    1800 tgtgctctcc ctcagtaccc tgataggcac tgtggctgag acatccaagg agaagtaccg    1860
cctgcttgac cagagagaca ggatcatgcg gcaagctcgg gtgaagagaa ccgatctgga    1920
caaagcgagg acttttgttg gcacctgcct ggatatgtgt cctgagaagg agaggtacat    1980
gcgggagacc cgtagccagc tgagcgtgtt cgaagtggtc ccagggactg accaggtgga    2040
ccacgcagca gctgtgaaag agtacagtcg gtcctcggcg gatcaggagg agcccctgcc    2100
ccacgagctg cggcccttgc cagtgctcag caggaccatg gactacctgg tgacccagat    2160
catggaccag aaggagggca gcctgcggga ttggtatgac ttcgtgtgga accgcacgcg    2220
tggcatacgg aaggatatca cgcagcagca cctctgtgac cccctgacgg tgtccctgat    2280
tgagaagtgc acccgtttc acatccactg tgcccacttc atgtgtgagg agcccatgtc    2340
ctcctttgat gccaagatca ataatgagaa catgaccaag tgcctgcaga gcctgaagga    2400
gatgtaccag gacctgagaa acaagggtgt cttctgtgcc agcgaagcgg agttccaggg    2460
ctacaatgtt ctgctcagtc tcaacaaggg agacatccta agagaagtac aacagttcca    2520
tcctgctgtt agaaactcat ctgaggtgaa atttgctgtt caggcttttg ctgcattgaa    2580
cagtaataat tttgtgagat ttttcaaact ggtccagtca gcttcttacc tgaacgcttg    2640
tcttttacac tgttacttca gtcagatccg caaggatgct ctccgggcgc tcaactttgc    2700
gtacacggtg agcacacagc gatctaccat ctttccctg gatggtgtgg tgcgcatgct    2760
gctgttcaga gactgtgaag aggccaccga cttcctcacc tgccacggcc tcaccgtttc    2820
cgacggctgt gtgagctga accggtctgc attcctggaa ccagagggat tatccaagac    2880
caggaagtcg gtgttatta ctaggaagct gacggtgtca gtcggggaaa ttgtgaacgg    2940
agggccattg ccccccgtcc ctcgtcacac ccctgtgtgc agcttcaact cccagaacaa    3000
gtacatcggg gagagcctgg ccgcggagct gcccgtcagc acccagagac ccggctccga    3060
cacagtgggc ggagggagag gagaggagtg tggtgtagag ccggatgcac ccctgtccag    3120
tctcccacag tctctaccag ccccctgcgcc ctcaccagtg cctctgcctc ctgtcctggc    3180
actgaccccg tctgtggcgc ccagcctctt ccagctgtct gtgcagcctg aaccaccgcc    3240
tccagagccc gtgcccatgt actctgacga ggacctggcg caggtggtgg acgagctcat    3300
ccaggaggcc ctgcagaggg actgtgagga agttggctct gcgggtgctg cctacgcagc    3360
tgccgccctg ggtgtttcta atgctgctat ggaggatttg ttaacagctg caaccacggg    3420
cattttgagg cacattgcag ctgaagaagt gtctaaggaa agagagcgaa gggagcagga    3480
gaggcagcgg gctgaagagg aaaggttgaa acaagagaga gagctggtgt taagtgagct    3540
gagccagggc ctgccgtgg agctgatgga acgcgtgatg atggagtttg tgagggaaac    3600
ctgctcccag gagttgaaga atgcagtaga cacagaccag agggtccgtg tggcccgttg    3660
ctgtgaggat gtctgtgccc acttagtgga cttgtttctc gtggaggaaa tcttccagac    3720
tgcaaaggag accctccagg agcttcagtg ctttctgcaag tatctacagc ggtggaggga    3780
agctgtcaca gcccgcaaga aactgaggcg ccaaatgcgg gctttccctg ctgcgccctg    3840
ctgcgtggac gtgagcgacc ggctgagggc gctggcgccc agcgcagagt gccccattgc    3900
tgaagagaac ctggccaggg gcctcctgga cctgggccat gcagggagat tgggcatctc    3960
```

-continued

```
ttgcaccagg ttaaggcggc tcagaaacaa gacagctcac cagatgaagg ttcagcactt    4020
ctaccagcag ctgctgagtg atgtggcatg ggcgtctctg gacctgccat ccctcgtggc    4080
tgagcacctc cctgggaggc aggagcatgt gttttggaag ctggtgctgg tgttgccgga    4140
tgtagaggag cagtccccag agagttgtgg cagaattcta gcaaattggt taaaagtcaa    4200
gttcatggga gatgaaggct cagtggatga cacatccagc gatgctggtg ggattcagac    4260
gctttcgctt ttcaactcac ttagcagcaa aggggatcag atgatttctg ttaacgtgtg    4320
tataaaggtg gcccatggcg ccctcagtga tggtgccatt gatgctgtgg agacacagaa    4380
ggacctcctg ggagccagtg ggctcatgct gctgcttccc cccaaaatga agagtgagga    4440
catggcagag gaggacgtgt actggctgtc ggccttgctg cagctcaagc agctcctgca    4500
ggctaagccc ttccagcctg cgcttcctct ggtggttctt gtgcctagcc caggagggga    4560
cgccgttgag aaggaagtag aagatggtct gatgctacag gacttggttt cagctaagct    4620
gatttcagat tacactgtta ccgagatccc tgataccatt aatgatctac aaggttcaac    4680
taaggttttg caagcagtgc agtggctggt ttcccactgc ccccattccc ttgacctctg    4740
ctgccagact ctcattcagt acgtcgaaga cgggattggc catgagttta gtggccgctt    4800
tttccatgac agaagagaga ggcgtctggg cggtcttgct tctcaggagc ctggcgccat    4860
cattgagctg tttaacagtg tgctgcagtt cctggcttct gtggtgtcct ctgaacagct    4920
gtgtgacctg tcctggcctg tcactgagtt tgctgaggca gggggcagcc ggctgcttcc    4980
tcacctgcac tggaatgccc cagagcacct ggcctggctg aagcaggctg tgctcgggtt    5040
ccagcttccg cagatggacc ttccacccct gggggccccc tggctccccg tgtgctccat    5100
ggttgtccag tacgcctccc agatccccag ctcacgccag acacagcctg tcctccagtc    5160
ccaggtggag aacctgctcc acagaaccta ctgtaggtgg aagagcaaga gtccctcccc    5220
agtccatggg gcaggcccct cggtcatgga gatcccatgg gatgatctta tcgccttgtg    5280
tatcaaccac aagctgagag actggacgcc ccccggcttc ctgttacat cagaggcgct    5340 gagtgaagat ggtcagatat gtgtgtattt ttttaaaaac gatttgaaaa aatatgatgt    5400
tcctttgtcg tgggaacaag ccaggttgca gacgcagaag gagctacagc tgagagaggg    5460
acgtttggca ataaagcctt tcatccttc tgcaaacaat tttcccatac cattgcttca    5520
catgcaccgt aactgaaaga ggagcacaga gtgtgctcaa gagggagga ttcccagcac    5580 agaggatctg atgcgaggag cttctgctga ggagctcttg gcgcagtgtt tgtcgagcag    5640
tctgctgctg gagaaagaag agaacaagag gtttgaagat cagcttcagc aatggttgtc    5700
tgaagactca ggagcattta cggatttaac ttcccttccc ctctatcttc ctcagactct    5760
agtgtctctt tctcacacta ttgaacctgt gatgaaaaca tctgtaacta ctagcccaca    5820
gagtgacatg atgagggagc aactgcagct gtcagaggcg acaggaacgt gtctaggcga    5880
acgactaaag cacctggaaa ggctgatccg gagttcaagg gaagaggaag ttgcctctga    5940
gctccatctc tctgcgctgc tagacatggt ggacatttga gcagcctgac ctgtggggag    6000
ggggtctctc ccgaagagtt tctgttttta ctcaaaataa tgttattctc agatgcttga    6060
tgcactgttg gaaatgtgat taatttaatc atgcagataa accatttaaa tgtc          6114
```

<210> SEQ ID NO 5
<211> LENGTH: 20
<212> TYPE: DNA
<213> ORGANISM: Artificial Sequence
<220> FEATURE:

```
<223> OTHER INFORMATION: Forward Primer

<400> SEQUENCE: 5
ccgtgggatg acatcatcac                                          20

<210> SEQ ID NO 6
<211> LENGTH: 20
<212> TYPE: DNA
<213> ORGANISM: Artificial Sequence
<220> FEATURE:
<223> OTHER INFORMATION: Reverse Primer

<400> SEQUENCE: 6
catgtccacc atctccagca                                          20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tttgtctgga ggatgatcgc                                          20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
aaagagaaag gggccaggcc                                          20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccagcttctt gtccaaaagc                                          20
```

GANP PROTEINS

This case is the National Stage Entry of application PCT/JP99/04634, filed Aug. 27, 2000, which claims priority to Japanese application JP 11/47035, issued Feb. 24, 1999.

TECHNICAL FIELD

The present invention relates to a novel protein having a kinase activity and a gene encoding said protein.

BACKGROUND ART

Antigen binding to the membrane IgR initiates the activation and maturation of the antigen-specific B cells in the peripheral lymphoid organs (Rajewsky, Nature (Lond.)., 381:751–758, 1996; Sakaguchi et al., Adv. Immunol. 54:337–392, 1993). B cells enter the outer periarterial lymphoid sheath (PALS) (Rajewsky, Nature (Lond.)., 381:751–758, 1996) and initiate costimulus-dependent interactions with specific Th cells and interdigitating dendritic cells within 48 h after immunization (MacLennan, Annu. Rev. Immunol. 12:117–139, 1994; Liu et al., Immunol. Rev. 156:111–126, 1997). Antigen-driven B cells proliferate in the outer PALS and then undergo further activation in the lymphoid follicles to establish the germinal center (herein sometimes abbreviated as GC) (Han et al., J. Immunol. 155:556–567, 1995; Jacob et al., J. Exp. Med. 176:679–687, 1992; Kelsoe, Immunity 4:107–111, 1996). Such B cells mature into large sIg$^-$ centroblasts that rapidly move through the cell cycle to form the dark zone and further mature into centrocytes that express a unique surface character of PNA$^+$ B220$^+$sIgM$^+$sIgD$^-$CD38$^-$ in the light zone of the GC (Kosco-Vilbois et al., 1997. Immunol. Today 18:225–230, 1997; Kelsoe, Immunol. Today 16:324–326, 1995; Oliver et al., J. Immunol. 158:1108–1115, 1997).

Centrocytes presumably undergo the processes of either apoptosis or affinity maturation of immunoglobulin V regions and the change process of class switching toward the IgG class antigen. Some centrocytes survive for a longer period in the lymphoid compartment as memory B cells. The other centrocytes probably migrate to the marginal zone of the GC and receive further antigenic stimulation and costimulatory signals through B cell activation molecules, such as CD40 and CD38, and receptors for various B cell stimulatory cytokines (Gray et al., J. Exp. Med., 180:141–155, 1994; Foy et al., J. Exp. Med., 180:157–163, 1994). Antigen-specific B cells further stimulated in this area probably migrate into the interstitial region of the spleen (called red pulp), where various kinds of other immune-competent cells may interact with antigen-driven B cells. Histochemical analysis in several autoimmune mice identified unique antibody-producing cells in this area which appear as plasma cells or aberrant plasma cells called Mott cells (Tarlinton et al., Eur. J. Immunol. 22:531–539, 1992; Jiang et al., J. Immunol., 158:992–997, 1997).

Autoimmunity is a phenomenon in which the impairment of self/nonself discrimination occurs frequently in the antigen-specific lymphocytes (Theofilopoulos, Immunol. Today, 16:90–98, 1995). The immune systems of various autoimmune diseases show the combinatory mechanism involving T cells and B cells (Theofilopoulos et al., Adv. Immunol., 37:269–290, 1985; Okamoto et al., J. Exp. Med. 175:71–79, 1992; Reininger et al., J. Exp. Med., 184:853–861, 1996; Theofilopoulos, et al., Immunol. Rev. 55:179–216, 1981; Watanabe-Fukunaga et al., Nature (Lond.)., 356:314–317, 1992; Takahashi et al., Cell, 76:969–976, 1994; Shlomchick et al., Nature (Lond.). 328:805–811, 1987).

NZB and NZW are the strains characterized by multiple genetic factors generating the severe autoimmune state of SLE as (NZB×NZW)F$_1$ mice (Theofflopoulos et al., Adv. Immunol., 37:269–290, 1985; Okamoto et al., J. Exp. Med., 175:71–79, 1992; Reininger et al., J. Exp. Med., 184:853–861, 1996; Theofilopoulos et al., Immunol. Rev., 55:179–216, 1981). NZB mice spontaneously generate the state of autoimmunity with the anti-red blood cell antibody that causes an autoimmune hemolytic anemia (Okamoto et al., J. Exp. Med., 175:71–79, 1992). NZW mice show an insidious autoimmune phenomenon (Reininger et al., J. Exp. Med. 184:853–861, 1996). The SLE state of (NZB×NZW) F$_1$ mice is apparently caused by multiple genetic factors associated with T and B cells (Theofilopoulos et al., Immunol. Rev., 55:179–216, 1981). NZB mice show an apparent abnormality of B cells, but the molecular mechanism of the abnormal B cell activation in NZB mice remains to be elucidated.

DISCLOSURE OF THE INVENTION

To address the issue of which molecules are involved in such maturation of B cells, the present inventors prepared monoclonal antibodies against intracellular components of a murine B cell line WEHI-231, which has the NZB genetic background. A monoclonal antibody named 29-15 recognizes a differentiation antigen whose expression is augmented in GC-B cells of peripheral lymphoid organs. With the 29-15 monoclonal antibody, the present inventors studied the expression of the antigen in peripheral lymphoid organs, which characterized the molecule as a differentiation antigen upregulated in the light zone of the GC from hyperimmunized mice. In the spleen of NZB mice, IgM-producing plasma cells with high expression of the GANP antigen appear before the onset of autoimmunity, which would suggest that this is an important molecular event for understanding the peripheral immune response and autoimmunity with autoantibodies.

The present inventors have studied to identify the above-mentioned antigen whose expression is selectively increased in centrocytes of germinal center, and confirmed by in situ RNA hybridization using an isolated cDNA probe (ganp probe) that the expression of ganp mRNA is increased in the area stained with 29-15 monoclonal antibody. It was also confirmed that the gene product, GANP protein, is a protein of 210 kD which is localized in cytoplasma and nucleus, and is structurally similar with a transcription regulating factor in yeasts, SAC3. When B cells are activated with anti-IgM antibody and anti-CD40 antibody, the amount of kinase which binds to GANP protein increased. These results suggests that GANP protein may be involved in a signal conversion of abnormal B cell differentiation in certain autoimmune state. The present invention has been completed on the basis of these findings.

Thus, the present invention provides a GANP protein represented by the amino acid sequence shown in SEQ ID No.1 or No.3 of the sequence listing. According to the present invention, there is provided a GANP mutant protein which is consisted of the amino acid sequence wherein one or more amino acids are deleted, one or more amino acids are substituted with other amino acid(s), and/or one or more other amino acids are added in the amino acid sequences shown in SEQ ID No.1 or No.3 of the sequence listing, and has a kinase activity similar with that of GANP protein. According to the present invention, there is provided a polypeptide which contains, as a partial sequence, a full length amino acid sequence of the aforementioned GANP protein or the aforementioned GANP mutant protein.

According to another aspect, the present invention provides a polynucleotide which encodes the aforementioned GANP protein or GANP mutant protein. The typical polynucleotide is DNA encoding GANP protein derived from mammal, and the DNA of mammal gene is preferred among them. Examples of most preferred polynucleotide are represented by the base sequences shown in SEQ ID No. 2 (DNA sequence encoding GANP protein from mouse) or SEQ ID No. 4 (DNA sequence encoding GANP protein from human) of the sequence listing.

Further, according to the present invention, there is provided an antisense polynucleotide which is composed of the base sequence of an antisense chain of the aforementioned polynucleotide, or derivatives of said antisense polynucleotide. Furthermore, according to the present invention, there is provided a polynucleotide or antisense polynucleotide of continuous 12 or more bases which is a partial sequence of the aforementioned polynucleotide or the aforementioned antisense polynucleotide, and a chemically modified polynucleotide or antisense polynucleotide of the aforementioned polynucleotide or the aforementioned antisense polynucleotide.

According to further another aspect, the present invention provides a method for obtaining DNA of the base sequence shown in SEQ ID No. 2 or No. 4 of the sequence listing or DNA which is the homologue from other mammal, wherein the aforementioned polynucleotide or antisense polynucleotide is used as a probe, and cDNA which hybridizes to the probe is obtained from mammal cDNA library. The length of the cDNA is almost the same as that of GANP gene, and the protein encoded by it has approximately 210 kDa. Further, according to the present invention, there is provided cDNA obtained by the aforementioned method and GANP protein encoded by it.

According to further another aspect of the present invention, there is provided an antibody which recognizes GANP protein or GANP mutant protein.

BRIEF DESCRIPTION OF THE DRAWINGS

FIG. 3 is a photograph showing appearance of 29-15+ cells in the GC area of SRBC-immunized mice. The sections of the GC area are stained with PNA, anti-BrdU, and the 29-15 mAb in combination with the individual colors as described in the Materials and Methods. Upper photograph shows hematoxylin staining of the GC area (GC) and the central artery (CA). Middle photograph shows three-color staining, indicating the 29-15+PNA+ cells. Lower panel shows a schema of 29-15+PNA+ cells.

FIG. 9 is a diagram showing a deduced amino acid sequence of mouse GANP protein in one character notation.

FIG. 13 is a diagram showing the results where spleen B cells from normal BALB/c mice were stimulated with F(ab')$_2$ of goat anti-lgM Ab (10 µg/ml) and anti-CD40 mAb (10 µg/ml) for 48 hour and stained with the anti-GANP mAb.

FIG. 14 is a diagram showing the results where in vitro kinase reaction was carried out with the anti-GANP immunoprecipitates in the presence of [γ-$^{32}$P]-ATP for 10 minutes. Phosphorylation on the proteins were detected by the autoradiography after SDS-PAGE separation. Phosphorylation of the GANP is indicated with an arrow (FIG. A), and phosphoamino acid analysis of phosphorylated GANP protein is also shown (FIG. B).

FIG. 20 is a scheme showing a result where double staining with anti-MCM3 Ab and anti-CR1 mAb, or PNA, was performed. The expression of MCM3 was upregulated in GC area.

FIG. 21 is a scheme where a deduced amino acid sequence of human GANP protein is represented in one character notation.

PREFERRED EMBODIMENT FOR CARRYING OUT THE INVENTION

Figure 1:
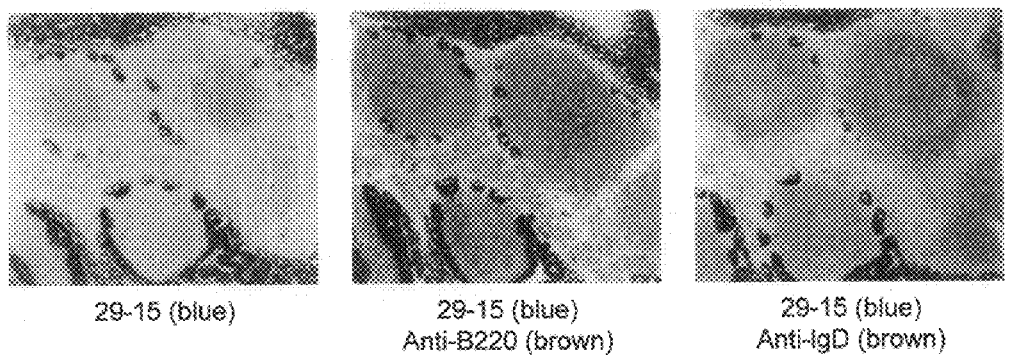
FIG. 1 is a photograph showing detection of 29-15+ cells in the PP of normal mice. The immunohistochemical analysis was carried out on PP with the 29-15 mAb and ALP-anti-rat Ig antibody. Positive cells appear in the central area with Vector Blue ALP substrate, and the strong signal in the surrounding area is in intestinal villi containing nonspecific endogenous ALP activity. For two-color staining, the sections are further stained either with biotin-anti-B220 mAb or biotin-anti-IgD mAb followed by HRP-streptavidin in combination with DAB.

The typical examples of GANP protein of the present invention are protein represented by the amino acid sequences of SEQ ID No. 1 and No. 3 of the sequence listing, and are characterized in that they have a molecular weight of 210 kDa and have a kinase activity. GANP mutant proteins provided by the present invention are represented by the amino acid sequences wherein approximately 1 to several, preferably 1 to 20, more preferably 1 to 10, most preferably 1 to 5 amino acid residues are substituted, inserted, and/or deleted in the amino acid sequences of SEQ ID No. 1 or No. 3, and have a kinase activity which is substantially similar with GANP protein represented by the amino acid sequences of SEQ ID No. 1 or No. 2. These GANP mutant proteins are within the scope of the present invention. The protein represented by the amino acid sequences of SEQ ID No. 1 or No. 3 of the sequence listing and homologue thereof are those whose expression is selectively increased in centrocytes of germinal center of mammal from which the protein is derived.

Usually, the active domain of GANP protein or GANP mutant protein can be readily identified by preparing a polypeptide wherein amino acid residue(s) are deleted from N-terminal and/or C-terminal of the full length amino acid sequence, and measuring the kinase activity of the polypeptide. The polypeptides provided by the present invention are those comprised of an active domain of GANP protein and GANP mutant protein and those comprising, as a partial sequence, a polypeptide comprised of said active domain, and have a kinase activity which is substantially similar with GANP protein. Moreover, another polypeptides provided by the present invention are those comprising, as a partial sequence, a full length amino acid sequence of GANP protein or GANP mutant protein, and have a kinase activity which is substantially similar with GANP protein.

The polynucleotide provided by the present invention includes DNA and RNA as well as all of the nucleotides obtained by chemically modifying DNA or RNA. The term "polynucleotide" used herein should be most broadly interpreted to include non-naturally occurring form. The typical examples of the polynucleotide provided by the present invention are DNA or RNA which encodes the aforementioned GANP protein or GANP mutant protein. Another example of the polynucleotide of the present invention is antisense polynucleotide.

It is well known for a skilled person in the art that, using degeneracy of genetic code, at least partial bases of a polynucleotide can be replaced with another type of bases without changing the amino acid sequence of the polypeptide which is produced from the polynucleotide. Therefore, the polynucleotide of the present invention includes all polynucleotides which encode GANP protein or GANP mutant protein. As examples of the preferred gene of the present invention, a gene encoding GANP protein from mouse is shown in SEQ ID No.2 of the sequence listing, and a gene encoding GANP protein from human is shown in SEQ ID No.4. The amino acid sequence of GANP mutant protein can be determined from the base sequence of a gene encoding said mutant. For example, sequencing can be carried out by using commercially available programs (for example, MacVector (registered trademark, Eastman Chemical), or Genetix (Software Kaihatsu)).

The scope of the present invention covers antisense polynucleotides composed of a base sequence of antisense chain of polynucleotide encoding GANP protein, and derivatives thereof. The antisense polynucleotides is provided as an embodiment of the polynucleotide mentioned above, and the term "antisense polynucleotide" may be herein used to clearly mean that it is a polynucleotide comprised of base sequence of antisense chain. The antisense polynucleotide can hybridize to polynucleotide encoding GANP protein, and if the polynucleotide to which it hybridize is a polynucleotide of coding region, the biosynthesis of the polypeptide encoded by the polynucleotide can be inhibited.

Antisense polynucleotide for inhibiting the biosynthesis of polypeptide preferably contains 12 or more bases. On the other hand, an unnecessarily long sequence is not preferred in order to incorporate full length antisense polynucleotide into cells. When an antisense polynucleotide is incorporated into cells to inhibit the biosynthesis of GANP protein, it is preferred to use an antisense polynucleotide of 12 to 30 bases, preferably 15 to 25 bases, more preferably 18 to 22 bases.

The antisense polynucleotide of the present invention or derivatives thereof include all of the form where several nucleotides composed of base, phosphoric acid and sugar are bound whether or not they are present in nature. Typical examples include a naturally occurring antisense DNA and antisense RNA. Non-naturally occurring polynucleotides include, for example, polynucleotides of methylphosphonate type and phosphorothioate type. As to the antisense polynucleotide of the present invention, various antisense polynucleotide derivatives which are excellent in binding ability to target DNA or mRNA, tissue selectability, cell permeation property, nuclease resistance, intercellular stability and the like, can be obtained by using an antisense technology available to a skilled person in the art.

Generally, in view of easiness of hybridization, it is preferred to design an antisense polynucleotide or derivatives thereof having a base sequence complementary with base sequence which forms a loop of RNA. Therefore, as to the antisense polynucleotide of the present invention and derivatives thereof, those which hybridize to loop region of RNA are preferred examples. Moreover, an antisense polynucleotide having a sequence complementary with a translation initiation codon and neighborhood thereof, ribosome binding site, capping site, or splicing site can generally be expected to exhibit high expression inhibition effect. Therefore, the antisense polynucleotide of the present invention or derivatives thereof having a sequence complementary with a translation initiation codon and neighborhood thereof, ribosome binding site, capping site, and/or splicing site of the gene encoding GANP protein are preferred example in view of expression inhibition effect.

Among the currently generally known polynucleotide derivatives, the derivatives where at least one of nuclease resistance, tissue selectability, cell permeation property and binding ability is enhanced, preferably include derivatives having a phosphorothioate bond as a skeleton structure. The polynucleotide of the present invention and derivatives thereof include derivatives having these function or structure.

Among the antisense polynucleotide of the present invention, naturally occurring type of antisense polynucleotide may be synthesized by using a chemical synthesizer or may be prepared by a PCR method using a DNA encoding GANP protein as a templeta. Polynucleotide derivatives such as methylphosphonate type or phosphorotioate type may usually be prepared by chemical synthesis. In this case, the procedure can be carried out according to an instruction attached with the chemical synthesizer, and the synthesized product thus obtained can be purified by HPLC method using reverse phase chromatography and the like.

Polynucleotide which is a polynucleotide encoding GANP protein of the present invention, antisense polynucleotide thereof, or a portion thereof (for example, polynucleotide composed of continuous 12 or more bases) can be used as a probe for screening a DNA encoding GANP protein from mammalian cDNA library. For such a purpose, a polynucleotide composed of a sequence of continuous 15 or more bases is particularly preferred. The polynucleotide used as a probe may be a derivative. Usually, it is recognized that a sequence having the aforementioned number or more of base is a specific sequence.

A DNA of continuous 12 or more bases in the base sequence of SEQ ID No. 2 or No. 4 of the sequence listing, or a polynucleotide which hybridizes to said DNA (antisense polynucleotide) can be used as a probe for screening a DNA encoding GANP protein from cDNA library or the like.

Also, a tissue which expresses mRNA from GANP gene can be detected by performing a Northern Blot hybridization on mRNA derived from various tissues by using a polynucleotide encoding GANP protein of the present invention, antisense polynucleotide thereof, or a polynucleotide of a portion thereof as a probe. Furthermore, a polynucleotide of 12 or more bases can be used as a primer for polymerase chain reaction (PCR), and a polynucleotide encoding GANP protein can be obtained by PCR. Also, the primer can be appropriately selected to clone any portion of GANP protein.

As to the cDNA library used in the screening using the aforementioned probe, one prepared from mRNA can be preferably used. A group of cDNA selected by random sampling from these cDNA library may be used as a sample for screening. A commercially available cDNA library can be used.

The cDNA which hybridizes to the above-obtained GANP gene is inserted into a suitable vector (for example, pGEX-4T-1 vector), and is introduced into a host (for example, E.coli) to prepare a transformant. The type of the vector and the type of the host are not particularly limited, and any suitable expression vector may be selected and used depending on the type of the host. As the host, bacterium such as E.coli, yeasts, or animal cells can be used. A method for obtaining a transformant by introducing a recombinant vector into a suitable host such as E.coli is not particularly limited, and any method available to a skilled person in the art may be applied.

The transformant into which the GANP gene of the present invention was introduced can be cultured to amplify a gene DNA or produce a protein, thereby producing GANP protein. The preparation and culturing of a transformant are described in various literatures and reports, and many methods have been developed and have been conventionally used in the art. Therefore, a skilled person in the art can easily prepare GANP protein on the basis of the base sequence described herein. The methods for introducing a gene into cells include calcium chloride method, lipofection method, protoplast method, and electroporation method.

Separation and purification of a protein of interest from the culture can be carried out by using any means available to a skilled person in the art in combination appropriately. For example, GANP protein of the present invention can be efficiently recovered and purified by performing procedures such as concentration, solubilization, dialysis, various chromatography and the like. More specifically, selection may be suitably made among immunoprecipitation, salting out, ultrafilteration, isoelectric point precipitation, gel fiteration, electrophoresis, various chromatography such as ion exchange chromatography, hydrophobic chromatography and antibody chromatography, chromatofocusing, adsorption chromatography, and reverse phase chromatography. By using a gene encoding GANP mutant protein, GANP mutant protein can be similarly prepared.

Also, GANP protein or GANP mutant protein can be prepared as a fused protein with another polypeptide. Such a fused polypeptide is within the scope of the present invention. The type of the polypeptide to be fused is not particularly limited, and includes, for example, a signal peptide which promotes an extracellular secretion. The preparation of such a fused protein may be carried out by using transformant. When a fused protein is used to prepare GANP protein or GANP mutant protein, a fused protein is treated with a chemical substance such as bromecyan or an enzyme such as protease, and the substance of interest which was cut out may be separated and purified.

Antibodies which recognize GANP protein or GANP mutant protein can be prepared by using GANP protein or GANP mutant protein of the present invention or partial polypeptide thereof. The antibody of the present invention can be prepared by any means of a conventional method in the art by immunizing a mammal with GANP protein or GANP mutation protein. It can be confirmed by Western blotting, ELISA, immunostaining (for example, measurement with FACS) or the like that the antibody recognizes GANP protein or GANP mutation protein of the present invention. As immunogens, there may used GANP protein or GANP mutant protein as well as a portion thereof bound to another carrier protein such as calf serum albumin. A portion of GANP protein or GANP mutation protein preferably contains 8 or more amino acid residues, and such a polypeptide may be synthesized by using, for example, a peptide synthesizer.

A monoclonal antibody which is produced from hybridoma prepared by using lymphocytes of immunized animals may be used as an antibody of the present invention. The process for the preparation of a monoclonal antibody is well known in the art and is conventionally used ("Antibodies, A Laboratory Manual" (Cold Spring Harbor Laboratory Press, 1988), Chapter 6). Moreover, a fragment of antibody having a antigen-antibody reaction activity and a chimera antibody may be used as an antibody of the present invention. GANP protein or GANP mutant protein of the present invention can be detected by a method using an antibody or a method using an antibody and an enzyme.

The present invention is illustrated in detail by the examples below, but the scope of the present invention is not limited to the examples below.

EXAMPLE

Example 1

Cloning of Mouse GANP Gene and Analysis of Expression

<Materials and Methods>

(1) Animals and Immunization

BALB/c mice and Lewis rats were purchased from Seac Yoshitomi Ltd. (Fukuoka). NZB, NZW, (NZB×NZW)$F_1$ mice (7 week old, female), MRL/lpr mice (8 week old, female), and B×SB mice (7 week old, male) were obtained from Japan SLC Co. (Shizuoka). Aged NZB mice (10 month old, female) were kindly gifted from Dr. Sachiko Hirose (Department of Pathology, Juntendo University School of Medicine). NOD mice (7 week old, male) were generously provided from Dr. Junichi. Miyazaki (Department of Nutrition and Physiological Chemistry, Osaka University Medical School). All animals were maintained in Center for Animal Resources and Development in Kumamoto University. BALB/c mice were immunized multiply with sheep red blood cells (Nippon Bio-Test Laboratories, Inc., Tokyo). The immunization was performed intravenously with 5-day interval and sections of the thymus, spleen, lymph node (LN), and Peyer's patches (PP) were prepared for the immunohistochemical analysis.

(2) Cells and Cell Culture

Splenic B cells from BALB/c mice were enriched as described previously (Nomura et al., Immunol. Lett. 45:195–203, 1995). These cells were cultured in RPMI-1640 medium (Gibco-BRL, Gaithersburg, Germany) containing 10% heat-inactivated FCS (Dainippon Pharmaceutical Co., Osaka, Japan), 5 mM L-glutamine (Biowhitteker, Walkersville, Md., USA), 100 U/ml penicillin, 100 μg/ml streptomycin, and 50 μM 2-ME at 37° C. in an incubator with 5% carbon dioxide.

(3) Establishment of the 29-15 Monoclonal Antibody (Hereinafter Referred to as "25-15 mAb")

The mAbs against a murine B cell line WEHI-231, which was established from a (BALB/c×NZB)$F_1$ mouse with mineral oil, were prepared by the method described previously (Kuwahara et al., J. Immunol. 152:2742–2752, 1994). Briefly, the cell lysate of WEHI-231 with the surface phenotype $sIgM^+sIgD^+B220^+$ was prepared with the hypotonic buffer in the absence of detergent and dialyzed against a phosphate buffered saline (PBS) in accordance with the method of Sakaguchi et al (Sakaguchi et al., EMBO (Eur. Mol. Biol. Organ.) J. 5:2139–2147, 1986). The cell lysate was immunized into the foot pads of Lewis rats in the complete Freund's adjuvant (CFA) (Difco Laboratories, Detroit, Mich., USA) and boosted twice in the incomplete Freund's adjuvant (IFA) (Difco Laboratories) at day 4 and day 8. After 9 days, the lymph node of popliteal and inguinal regions were excised and the lymphoid cell suspension was prepared. Establishment of hybridomas, selection in the HAT media (Gibco-BRL), and recloning of hybridoma clones were performed as described previously (Kuwahara et al., J. Immunol. 152:2742–2752, 1994). The 29-15 mAb was selected to stain lymphoid cells in the immunohistochemical analysis.

(4) Antibodies and Reagents $F(ab')_2$ fragment of the affinity-purified goat anti-mouse μ antibody (ICN Pharmaceutical, Inc., Costa Mesa, Calif., USA), biotin-conjugated peanut agglutinin (PNA) (Vector Laboratories, Inc., Burlingame, Calif., USA), biotin-conjugated anti-CD35 mAb (PharMingen, San Diego, Calif.), alkalinephosphatase (ALP) conjugated goat anti-rat IgAb (#59301, ICN), HRP conjugated goat anti-rat IgAb (ICN), HRP conjugated streptavidin (Kirkegaard & Perry Laboratories, Inc., Gaitherburg, Md.), ALP conjugated goat anti-mouse IgAb (Sigma Chemicals Co., St. Louis, Mich.), FITC conjugated mouse anti-rat κ mAb (ICN), PE conjugated anti-B220 mAb (PhaMingen), and ALP conjugated goat anti-rabbit IgAb (Zymed Laboratories Inc., South San Francisco, Calif.) were purchased and used. Biotin-conjugated mAbs such as anti-B220 (RA3-6B2), anti-μ (AM/3), and anti-δ (CS/15) were prepared in our laboratory. Anti-CD40 mAb (LB429) was established in our laboratory (Nomura et al., Immunol. Lett. 45:195–203, 1995). Hybridomas of AM/3 and CS/15 were kindly provided by Dr. Kensuke Miyake (Department of Immunology, Saga Medical School). Biotin-conjugated anti-Syndecan-1 was purchased from PharMingen (San Diego, Calif., USA). Anti-BrdU mAb was obtained from Novocastra Laboratories, Ltd. (Newcastle, United Kingdom). Rabit anti-mouse MCM3/P1 Ab is described in the literature (Kimura, H et al, 1994, EMBO J. 13, 4311–4320).

(5) Immunohistochemistry

Immunohistochemical staining was performed as described previously (Ezaki et al., Arch. Histol. Cytol. 58:104–115, 1995; Yamanouchi et al., Eur. J. Immunol. 28:696–707, 1998). In brief, the target organs excised from BALB/c, NZB, (NZB×NZW)$F_1$, NOD, B×SB, and MRL/lpr mice were placed in OCT compound (Miles Inc., Elkhart, Ind., USA). The 6-μm cryosections placed on the gelatin-coated slides were air-dried fully. The slides were then fixed in acetone for 10 minutes, followed by rehydration in PBS for 15 minutes. The slides were incubated with the 29-15 mAb for 60 minutes and were washed with PBS several times. After incubation with alkaline phosphatase-conjugated goat anti-rat Ig antibody (ALP-anti-rat Ig, catalogue #59301, ICN Pharmaceutical, Inc.), the slides were washed four times with PBS. The slides were developed using Vector Blue (Vector Laboratories).

For secondary staining, the slides were incubated with biotin-labeled mAbs in combination with horseradish peroxidase (HRP)-conjugated streptavidin (Kirkegaard & Perry Laboratories, Inc., Gaithersburg, Md., USA). After development with p-dimehylaminoazobenzene (DAB, Dojindo, Kumamoto), the sections were fixed lightly with 1% glutaraldehyde solution in PBS. To detect the cells of active proliferation in vivo, BrdU (Sigma Chemicals Co., St. Louis, Mo., USA) was injected intravenously 1 hour before obtaining the organs. Cells undergoing DNA synthesis were detected by staining with anti-BrdU mAb in combination with ALP-conjugated goat anti-mouse Ig Ab (Sigma Chemicals Co.) followed by development with Vector Red (Matsuno et al., Cell Tissue Res. 257:459–470, 1989). Periodic acid Schiff (PAS) staining was performed as described previously (Jiang et al., J. Immunol. 158:992–997, 1997). All sections were mounted by Aquatex (E. Merck, Darmstadt, Germany).

(6) Molecular Cloning of the cDNA Using λgt11 Vector

The cDNA libraries constructed with mRNAs from the mouse spleen, mouse bone marrow, WEHI-231 cells and A20 cells were screened with the supernatant of the 29-15 mAb after transferring the fusion protein onto nitrocellulose filters (Schleicher and Schuell, Darmstadt, Germany) that were presoaked with 20 mM IPTG (Inui et al., J. Immunol. 154:2714–2723, 1995). The phage plates were incubated for 4 hours at 42° C. and then the plates were covered with the filters and further incubated for 4 hours at 37° C. The filters were washed three times with the washing buffer (PBS containing 0.1% Tween 20), blocked for 1 hour in the blocking buffer (5% nonfat dry milk in PBS containing 0.1% Tween 20), and then incubated with the 29-15 mAb. Positive signals were detected by autoradiography using $^{125}$I-labeled sheep anti-rat Ig Ab (Amersham, Buckinghamshire, United Kingdom). The initial cDNA clone contained a 280-bp fragment that is capable of coding a polypeptide as a fusion protein. With the original 280-bp fragment, the longer cDNA clones were isolated from another WEHI-231 cDNA library. The 4.9-kb fragment of the second cDNA clone encodes a longest open reading frame of 4.5 kb. To further determine the 5' sequence, the 5'-RACE method was employed. The race kit of Gibco-BRL was used.

(7) In Situ RNA Hybridization on Tissue Sections

In situ RNA hybridization was carried out as described previously (Kondo et al., Blood 80:2044–2051, 1992). Paraffin-embedded sections were mounted on silanized slides. After the slides were deparaffinized, hybridization with ganp 280-bp riboprobe labeled by digoxigenin was performed for 16 hours at 50° C. The slides were washed with TNE buffer (10 mM Tris-HCl [pH 7.6], 500 mM NaCl, 1 mM EDTA) at 37° C. several times, followed by washing with 2× and/or 0.2×SSC solution at 50° C. While using anti-digoxigenin antibody, the development was performed in the presence of ALP substrate.

(8) Preparation of GST-cDNA Fusion Protein and Another Anti-GANP mAb

The ganp cDNA fragment encoding a part of GANP (amino acids of 679th to 1028th of the amino acid sequence of SEQ ID No.1 of the sequence listing) was introduced into a pGEX-4T-1 vector (Pharmacia Biotech, Piscataway, N.J., USA). The recombinant plasmid was verified by DNA sequencing of the entire insert and the junction. The GST-GANP fusion protein was prepared by glutathione-Sepharose (Pharmacia) column chromatography as described elsewhere (Inui et al., J. Immunol. 154:2714–2723, 1995). Anti-GANP mAb, designated 42-23, was established by immunizing the fusion protein in rats as described above.

(9) Western Blot Analysis

Protein gel electrophoresis, Western blot transfer, and the immunodetection of proteins were performed as described previously (Kuwahara et al., Int. Immunol. 8:1273–1285, 1996). Fifty million cells were lysed with 1 ml of the TNE lysis buffer (10 mM Tris-HCl [pH 7.8], 150 mM NaCl, 1 mM EDTA, 1% NP-40, 0.02% NaN$_3$) and the immune complex was analyzed on SDS-PAGE (7%). After the proteins were transferred onto a nitrocellulose filter, the filter was blocked with PBS-Tween 20 containing 5% nonfat dry milk and incubated with anti-GANP mAb for 60 minutes. After washing with PBS-Tween 20 several times, the filter was incubated with HRP-conjugated goat anti-rat Ig (ICN Pharmaceutical, Inc.) for 30 minutes. The development was performed using an ECL detection kit (Amersham).

(10) Subcellular Fractionation

Separation of intact nuclei was carried out as described previously (Schriber et al., Nucleic Acids Res. 17:6419, 1989). WEHI-231 cells were washed with TBS and the pellets were resuspended in buffer A (10 mM HEPES [pH 7.9], 10 mM KCl, 0.1 mM EDTA, 0.1 mM EGTA, 1 mM DTT, 0.5 mM PMSF) and incubated for 15 minutes on ice, followed by the addition of NP-40 to a final 1%. After the centrifugation, the supernatants were recovered as a cytoplasmic fraction. The pellets were resuspended with the same buffer and homogenized to obtain the intact nuclei by staining. The sample was centrifuged and the pellet was resuspended with cold buffer C (20 mM HEPES [pH 7.9], 0.4 M NaCl, 1 mM EDTA, 1 mM EGTA, 1 mM DTT, 1 mM PMSF) and centrifuged. The supernatants were frozen at −80° C. as a nuclear fraction.

(11) In Vitro Kinase Reaction and Phosphoamino Acid Analysis

Kinase reaction was carried out in vitro with the immunoprecipitate as described previously (Kuwahara et al., J. Immunol. 152:2742–2752, 1994). Splenic B cells were purified by the method described (Nomura et al., Immunol. Lett. 45:195–203, 1995). The B cells were stimulated in vitro for 48 hours with F(ab')$_2$ fraction of goat anti-lgM Ab and anti-CD40 mAb (LB429) as described previously (Nomura et al., Immunol. Lett. 45:195–203, 1995). After harvesting and washing, cells were lysed with TNE lysis buffer and immunoprecipitated with the anti-GANP mAb (42-23). The immunoprecipitates were incubated with [γ-$^{32}$P]-ATP (Amersham) and the radiolabeled proteins were analyzed on SDS-PAGE (7%) and with autoradiography. The band corresponding to GANP was excised from dried gel. After SDS was removed from the gel, the homogenized gel was digested by TPCK-trypsin (Sigma Chemicals Co.) at 37° C. overnight. The samples were subjected to hydrolysis with 6N HCl and electrophoresed onto TLC (E. Merck).

V8 cleavage mapping of the indicated proteins was carried out as described previously (Kuwahara, K., et al, 1994, J. Immunol. 152:2742–2752).

(12) Cytoplasmic Staining

The cells were fixed with 2.5% paraformaldehyde solution in PBS followed by permeabilization with 70% ethanol for 1 hour on ice. The cells were incubated with the 29-15 mAb in combination with FITC-conjugated mouse anti-rat κ mAb. Antibody-binding was analyzed on FACScan flow cytometer (Becton-Dickinson, Mountain View, Calif., USA).

(13) Immunoprecipitation and Western Blot Analysis

Proteins obtained in the aforementioned (10) subcellular fractionation were immunoprecipitated with the anti-GABP mAb in combination with protein G-Sepharose, and analyzed by SDS-PAGE. The Western blot filter was incubated with the anti-GANP mAB, followed by HRP-anti-rat Ig. The development was performed using an ECL detection kit (Amersham).

(14) Reverse Transcriptase-PCR (RT-PCR)

Total RNA(1 μg each), purified from cultured B cells using TRISOL (Gibco BRL, Rockville, Md.) was used as a template for the cDNA synthesis (100 μl volume) with Superscript (Gibco BRL). PCR amplification was carried out using 2 μl of each cDNA solution with Taq-Gold (Perkin-Elmer, Foster, Calif.) and the primers for ganp or HPRT (control) (Han, S., et al, 1996, Science. 274–2092–2097). The ganp transcripts were amplified by 5'-CCGTGGGATGACATCATCAC-3' (the forward primer) (SEQ ID No. 5 of the sequence listing) and 5'-CATGTCCACCATCTCCAGCA-3' (the reverse primer) (SEQ ID No. 6 of the sequence listing).

<Results>

(1) Expression of the GANP Antigen in Lymphoid Organs

An mAb that recognizes a differentiation antigen expressed in peripheral B cells was prepared by immunizing rats with the lysate of WEHI-231 cells. Immunohistochemical analysis with the 29-15 mAb on normal lymphoid organs of BALB/c mice did not detect expression in the bone marrow, but showed the slight expression in lymphoid organs such as the thymus, spleen, and lymph node. A small number of cells in the red pulp of the spleen and the deep cortex of the lymph node strongly express the 29-15 Ag. Interestingly, the expression was very high in the central area of follicles of the PP (FIG. 1). The cells were positive with anti-B220 mAb, but not with anti-IgD mAb. Normal mice show the development of secondary lymphoid follicles with clear GC in PP because of the continuous stimulation of various antigenic substances introduced through the intestinal lumen.

Figure 2:
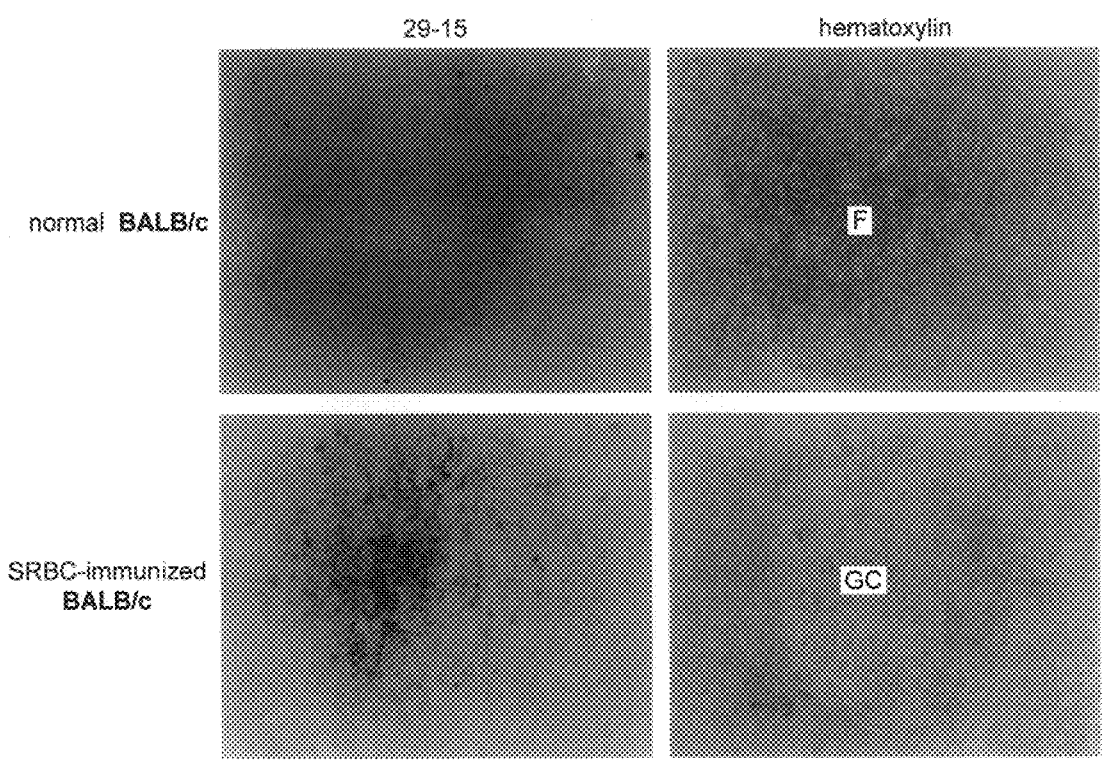
FIG. 2 is a photograph showing appearance of 29-15+ cells in the GC area of SRBC-immunized mice. Normal BALB/c mice were injected four times with SRBC during 12 days and the spleen sections were stained with hematoxylin or studied by immunohistochemistry as in FIG. 1. The sections of normal and SRBC-immunized BALB/c mice are parallel, when compared after staining with the 29-15 mAb.

Repeated immunization with sheep red blood cell (SRBC) induces the formation of lymphoid follicles in the spleen within 12 days. Antigen immunization induces an appearance of 29-15$^+$ cells in the GC area of the spleen and lymph node as well as in the GC of the PP (FIG. 2). The 29-15 antigen appeared upregulated in cells of the GC. The phenotype of 29-15$^+$ cells in the architecture of secondary lymphoid follicles was further analyzed. Nearly half of PNA$^+$ GC-B cells are positive with the 29-15 mAb, but they are negative with anti-BrdU mAb (FIG. 3). Interestingly, the expression of 29-15 Ag is upregulated in the centrocyte area at the distal region of the entrance from the central artery. This phenotype is consistent with the criteria of GC-B cells and supports the name "GANP" for the 29-15 Ag as described above.

Figure 4:
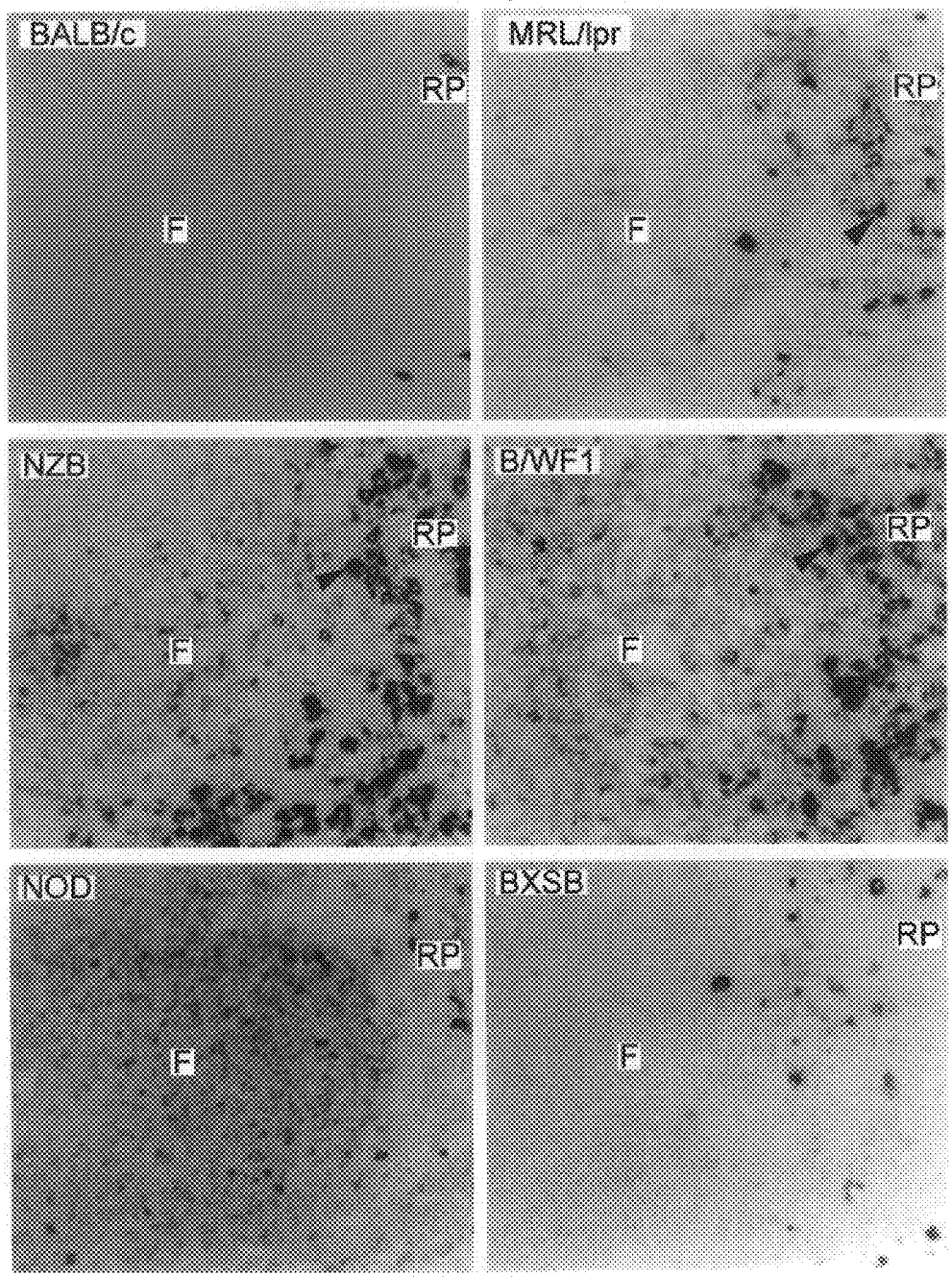
FIG. 4 is a photograph showing expression of the GANP$^{dense+}$ cells in the red pulp area of autoimmune-prone mice. Sections were prepared from the spleens of nonimmunized mice of BALB/c, NOD, NZB, (NZB×NZW)F$_1$, B×SB, and MRL/lpr. All mice were used 6–8 weeks after birth. The GANP$^{dense+}$ cells stained with the 29-15 mAb appear in the red pulp area of NZB, (NZB×NZW)F$_1$, MRL/lpr, and B×SB strains.

(2) Appearance of GANP$^{dense+}$ B Cells in the Red Pulp Area of Autoimmune-prone NZB Mice Normal mice express few GANP$^+$ B cells in the follicular area of the spleen without in vivo stimulation but show a few GANP$^{dense+}$ cells which remarkably express GANP protein in the red pulp area of BALB/c (FIG. 2) and C57BL/6. These cells are large and obviously different from conventional B cells. In young (8 week old) NZB mice, however, these GANP$^{dense+}$ cells increased spontaneously in the red pulp area of the spleen without immunization (FIG. 4). Another autoimmune-prone mouse, NZW, does not express GANP$^{dense+}$ cells in the red pulp at ages of 5 to 12 weeks. A severe-disease combination of (NZB×NZW)F$_1$ shows an intermediate expression of GANP$^{dense+}$ cells in the red pulp.

Figure 5:
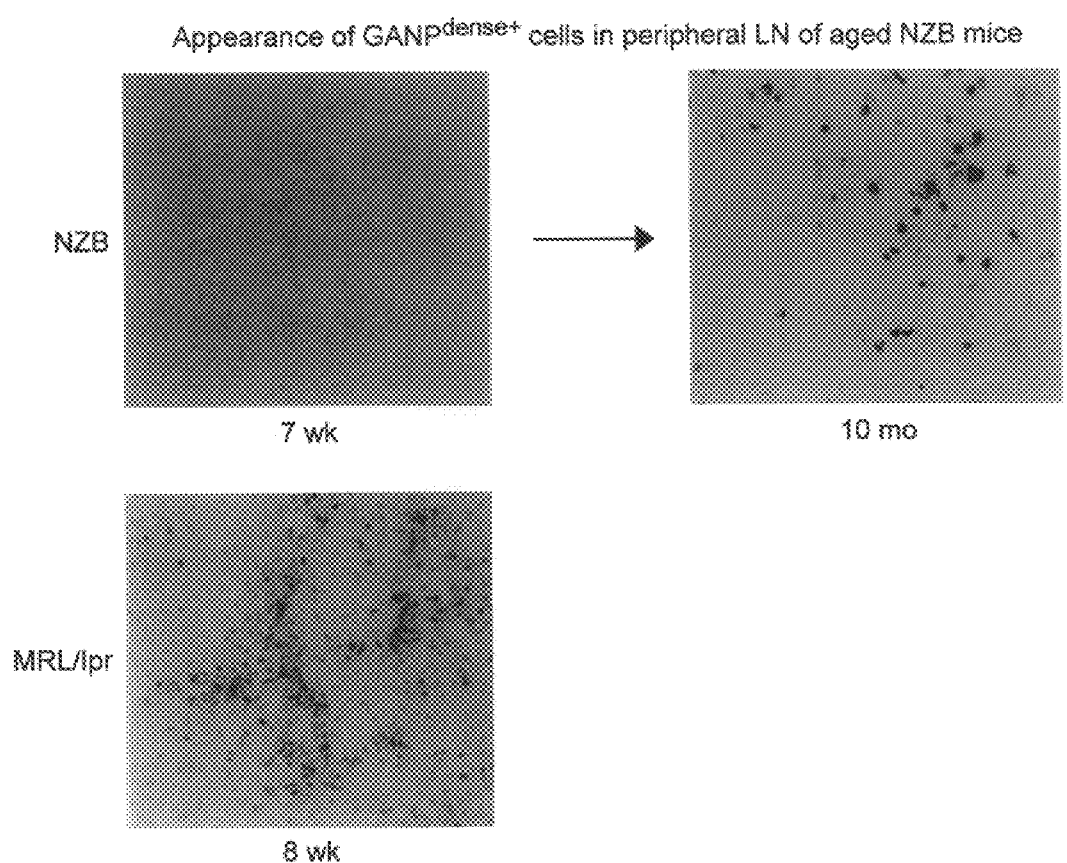
FIG. 5 is a photograph showing expression of the GANP$^{dense+}$ cells in the red pulp area of autoimmune-prone mice. Sections of the LN of popliteal regions were stained with the 29-15 mAb. The GANP$^{dense+}$ cells appear in peripheral LN of older NZB mice (10 month old) and MRL/lpr mice (8 week old).

Whether the GANP$^{dense+}$ cells also appear spontaneously in the spleen of other autoimmune-prone mice was examined. The GANP$^{dense+}$ cells appear in the spleen of B×SB and MRL/lpr, but not markedly in NZW and NOD mice at a similar age in the specific pathogen free condition (SPF). The GANP$^{dense+}$ cells become apparent during aging and appear in the peripheral lymph node of the aged-NZB mice (10 month old) that have passed the onset of the disease. The appearance of the GANP$^{dense+}$ cells in the lymph node seems to be mostly in the later stage. Of particular interest, MRL/lpr shows the appearance of GANP$^{dense+}$ cells in the lymph node at the young stage (8 week old) (FIG. 5). These results suggested that a genetic factor in autoimmune-prone NZB, B×SB, and MRL/lpr mice might control the appearance of GANP$^{dense+}$ cells in the red pulp area and the recruitment into the lymph node.

Figure 6:
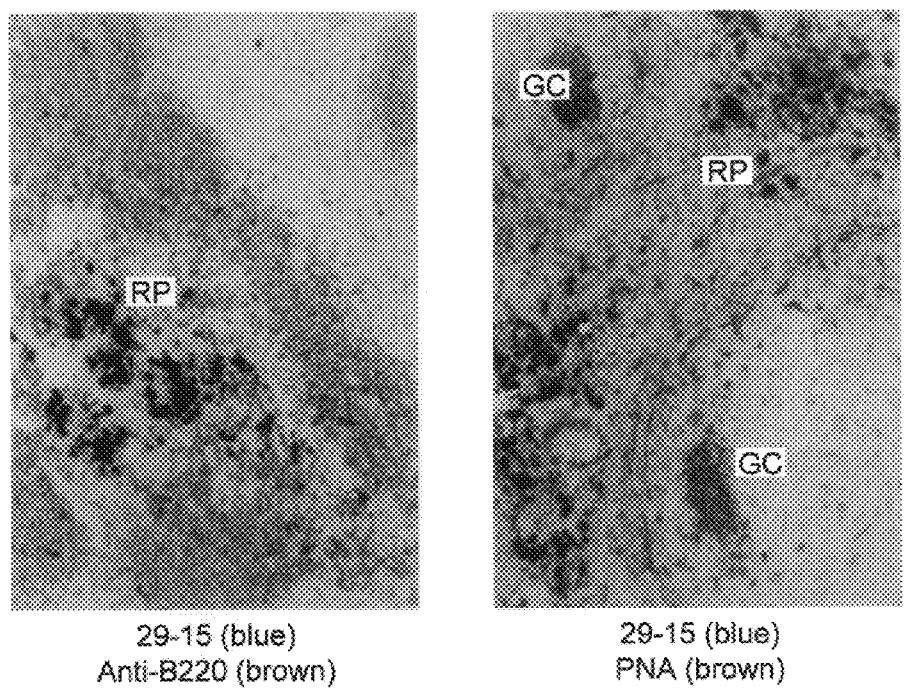
FIG. 6 is a photograph showing characterization of the GANP$^{dense+}$ cells in the autoimmune-prone mice. Sections were prepared with the spleen of nonimmunized NZB mice (8 week old). Immunohistochemical analysis was performed with the 29-15 mAb in combination with one of the following reagents: anti-B220, PNA.
Figure 7:
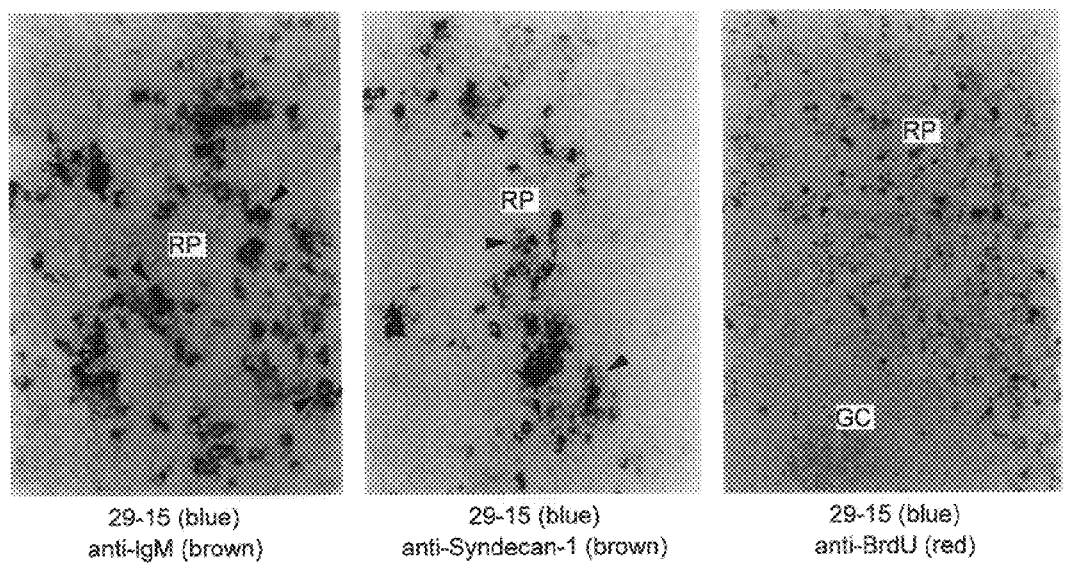
FIG. 7 is a photograph showing characterization of the GANP$^{dense+}$ cells in the autoimmune-prone mice. Sections were prepared with the spleen of nonimmunized NZB mice (8 week old). Immunohistochemical analysis was performed with the 29-15 mAb in combination with one of the following reagents: anti-lgM, anti-Syndecan-1, or anti-BrdU mAb.
Figure 8:
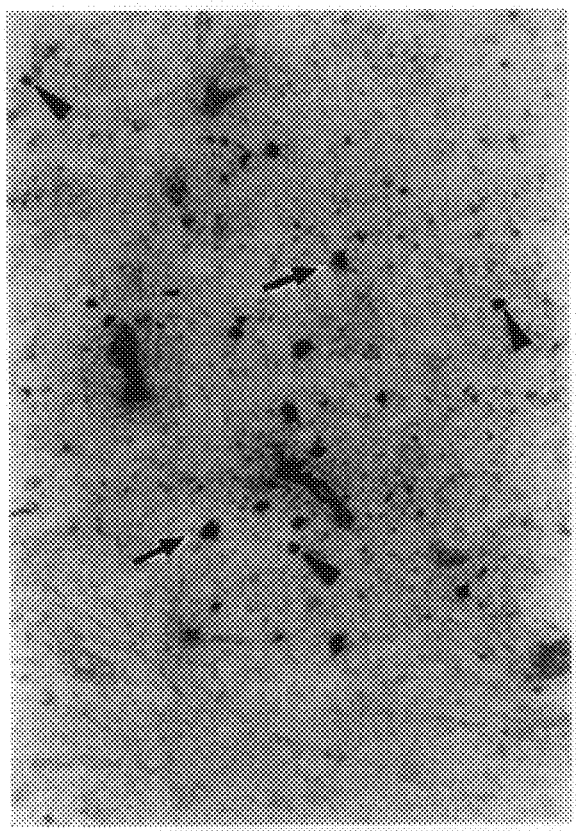
FIG. 8 is a photograph showing Mott cells that appear in NZB mice by PAS staining.

Two-color analysis showed the phenotype of GANP$^{dense+}$ cells in the red pulp area as PNA$^-$B220$^-$ cells (FIG. 6) and IgD$^-$CD38$^-$ cells. These cells are positive when stained with anti-Syndecan-1 mAb, which stains plasma cells selectively. The GANP$^{dense+}$ cells express IgM in cytoplasm (FIG. 7). Because these cells could be Mott cells (Jiang, Y., S. Hirose, Y. Hamano, S. Kodera, H. Tsurui, M. Abe, K. Terashima, S. Ishikawa and T. Shirai. 1997. J. Immunol. 158:992–997), the section was stained with PAS staining. The GANP$^{dense+}$ cells show PAS$^-$, as with the B220$^-$Syndecan-1$^+$PNA$^-$BrdU$^-$GANP$^{dense+}$ (FIG. 8) and CD40$^-$CD38$^-$. These plasma-like cells appear preferentially in the spleen of NZB mice, but are different from Mott cells currently reported.

(3) Identification of a cDNA Clone Encoding the GANP Antigen

Using the 29-15 mAb, we isolated a candidate cDNA clone (with the insert DNA of 280 bp) from the WEHI-231 cDNA library and further isolated a longer cDNA clone, named ganp. The full-length nucleotide sequence (6429 bp) determined from overlapping clones shows a putative polypeptide composed of 1971 amino acids with a predicted molecular size of 210-kD (FIG. 9). The amino acid sequence of GANP protein is shown in SEQ ID No.1 of the sequence listing and the base sequence of ganp cDNA is shown in SEQ ID No.2 of the sequence listing.

Figure 15:
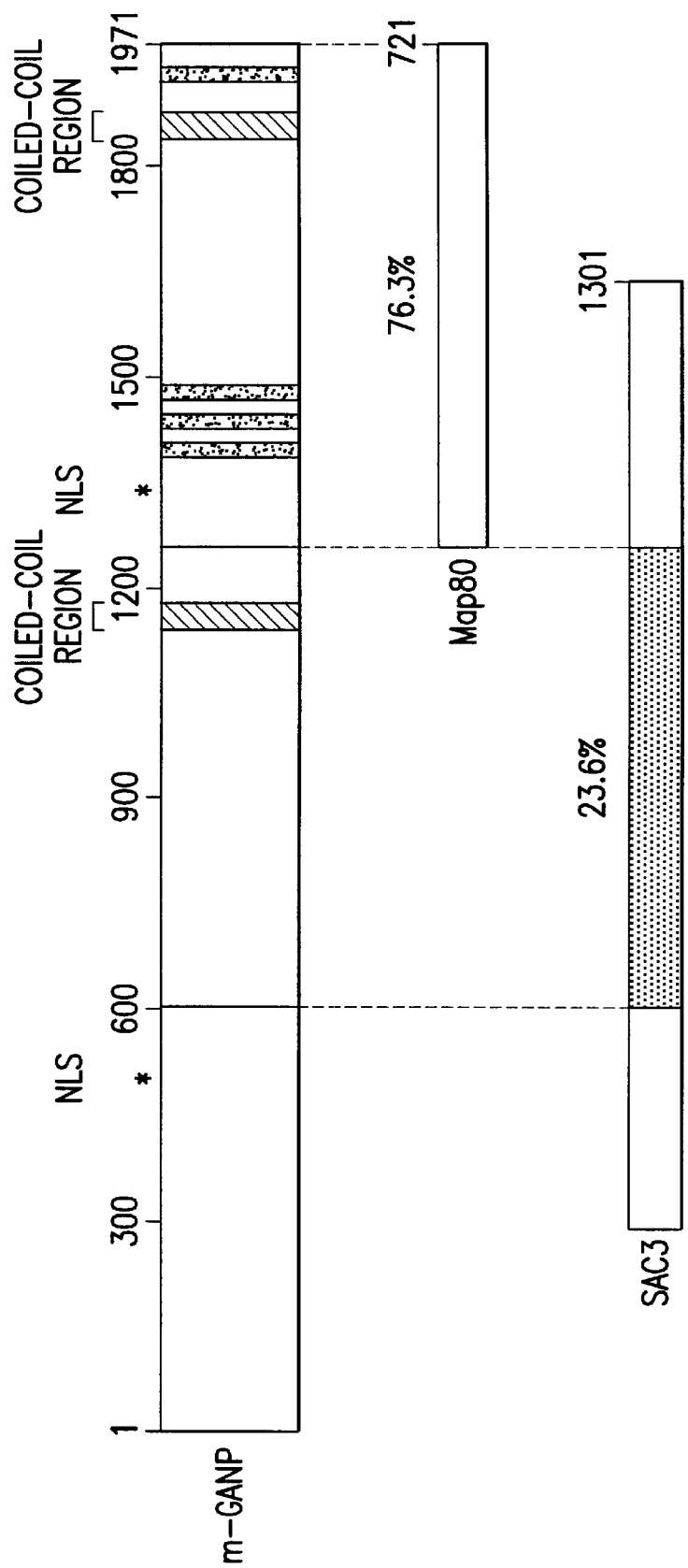
FIG. 15 is a diagram of the structure of the mouse GANP protein. In the figure, the homologous region to SAC3 and Map80, nuclear localization sequences (NLSs), and coiled-coil regions are indicated. Four LXXLL motifs are indicated by black.

The GANP amino acid sequence shows a regional homology to SAC3 which is considered to be a nuclear transcription regulation factor characterized in temperature-mutant *Saccharomyces cerevisiae* and human Map 80 protein (Takei, Y et al, 1998, J. Biol. Chem. 273:22177–22180) (FIG. 10 and FIG. 15; Bauer, A. and R. Koelling. 1996. Yeast 12:965–975). The GANP protein shows mild homologies within short stretches of the insulin promoter factor (amino acids 996 to 1063) and various transcription factors, including NF-IL-6 (amino acids 388 to 450).

The GANP gene shows a consensus base sequence for the super coil motifs, but does not show zinc-finger, leucine-zipper, and homeo-domain motifs. A serine/threonine-rich region was seen in N-terminal 100 amino acids, which has slight homology to nucleoporin, which is known as the nuclear pore complex. GANP has two possible nuclear localization sequences ($^{497}$HKKK and $^{1344}$PMKQKRR), which would potentially support the expression of the GANP in the nucleus as suggested by the PSORT program. Moreover, GANP has 2 coiled-coil motifs, but does not have zinc-finger, leucine-zipper, and homeo-domain motifs. Further, there were 4 LXXLL motifs which were recognized in nuclear transcription coactivator molecules including CBP/p300 and p/CIP (Torchia, J. et al., 1997. Nature (Lond.) 387:677–684; Heery et al., 1997, Nature (Lond.) 387:733–736), but any association molecule through these motif. has not been identified.

(5) Expression of the Ganp Transcripts

Figure 11:
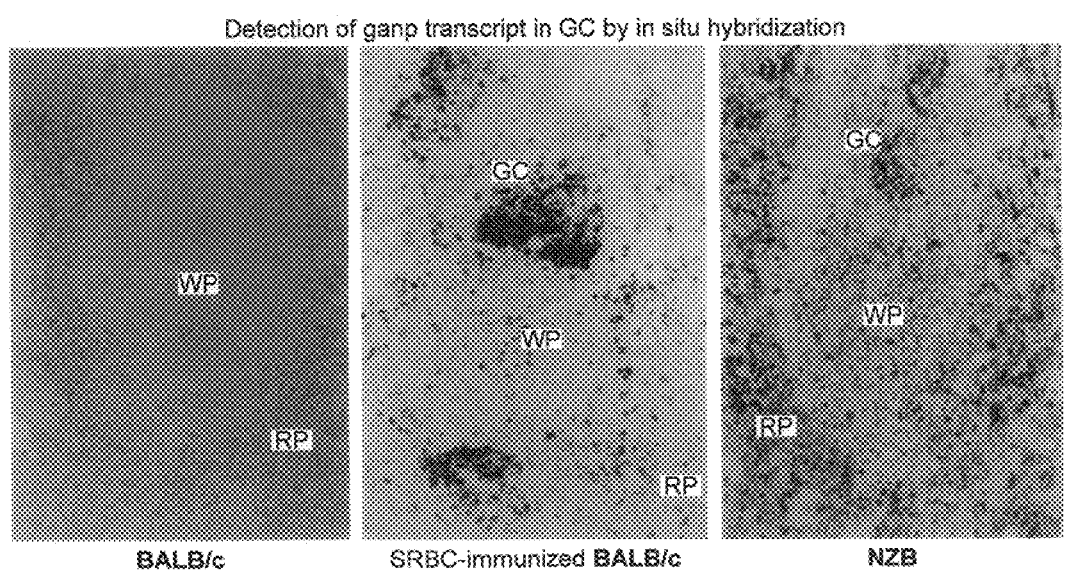
FIG. 11 is a photograph showing a result of in situ RNA hybridization of the ganp gene. Sections of spleens from SRBC-immunized, nonimmunized BALB/c, and NZB mice were hybridized with the ganp anti-sense probe. In the figure, the white pulp area (WP), red pulp area (RP), and GC area (GC) are indicated. The GANP$^{dense+}$ cells were recognized in the red pulp of NZB mice.

Northern blot analysis detected the 7-kb mRNA as a very weak signal in comparison to the control β-actin signal, but its expression was rather ubiquitous in all cell lines, organs, and tissues tested. In order to examine whether the ganp mRNA is upregulated in the same areas as detected on sections with the 29-15 mAb, in situ RNA hybridization analysis was carried out. The ganp mRNA is expressed abundantly in the central area of the GC of the SRBC-immunized spleen, but not in the nonimmunized spleen (FIG. 11), thymus, and lymph node. The ganp mRNA was upregulated in GC-B cells of immunized mice. This expression pattern is quite similar to the results with the 29-15 mAb on the same section based on staining with hematoxylin. The GC area of the PP also showed upregulation of the ganp mRNA in nonimmunized BALB/c mice, and the expression of ganp mRNA is high in plasma-like cells of the red pulp area of the spleen of nonimmunized NZB mice (FIG. 11). These results suggests that the ganp gene encodes a molecule recognized by the 29-15 mAb.

(6) Expression of the GANP in B Cells

Figure 12:
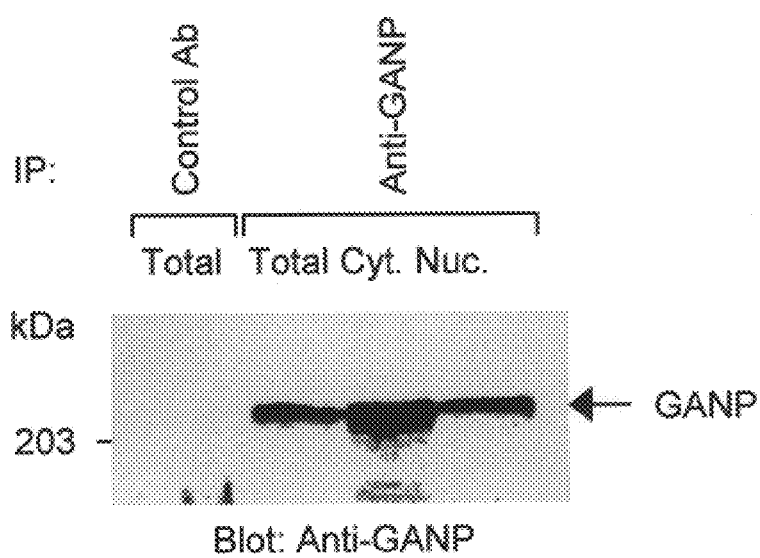
FIG. 12 is a diagram showing the results of the analysis by Western blotting after immunoprecipitation of GANP protein. The GANP protein was detected as a 210-kD protein expressed in cytoplasmic and nuclear fractions of WEHI-231 cells.

The anti-GANP mAb (42-23) detected a single protein band at 210-kD from both nuclear and cytoplasmic compartments of WEHI-231 cells (FIG. 12). In order to find evidence of the functional involvement of the GANP in the activation and differentiation of B lineage cells, B cells from nonimmunized BALB/c mice were stimulated in vitro with anti-IgM and anti-CD40 in combination, and as a result, an expression -of the GANP protein detected with the anti-GANP mAb was increased (FIG. 13). An in vitro kinase reaction with the GANP immunoprecipitates showed an increased kinase activity assembled with the GANP protein in spleen B cells stimulated in vitro. Thus, the GANP protein is inducibly phosphorylated at the serine/threonine residues (FIG. 14). These results suggest that the GANP might play a role to the activation of B cells in peripheral immune responses.

Figure 16:
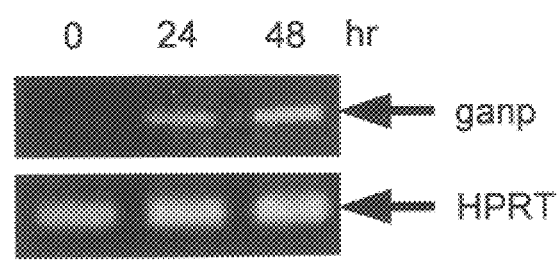
FIG. 16 shows a result of RT-PCR assay. The upregulation of gnap mRNA in anti-μ- and anti-CD40-stimulated B calls in vitro is shown. HPRT was used as a control to confirm the amount of each template.

Stimulation with anti-$\mu$ Ab and anti-CD40 mAb showed maximal response, but either one of these regents showed only a marginal response (data not shown). This upregulation was also detected by the increase of ganp mRNA in B cells stimulated by anti-$\mu$ and anti-CD40 co-ligation in vitro (FIG. 16). RT-PCR clearly demonstrated that the amount of ganp mRNA increased at 24 hours and 48 hours after stimulation in comparison with the control HPRT mRNA.

Figure 17:
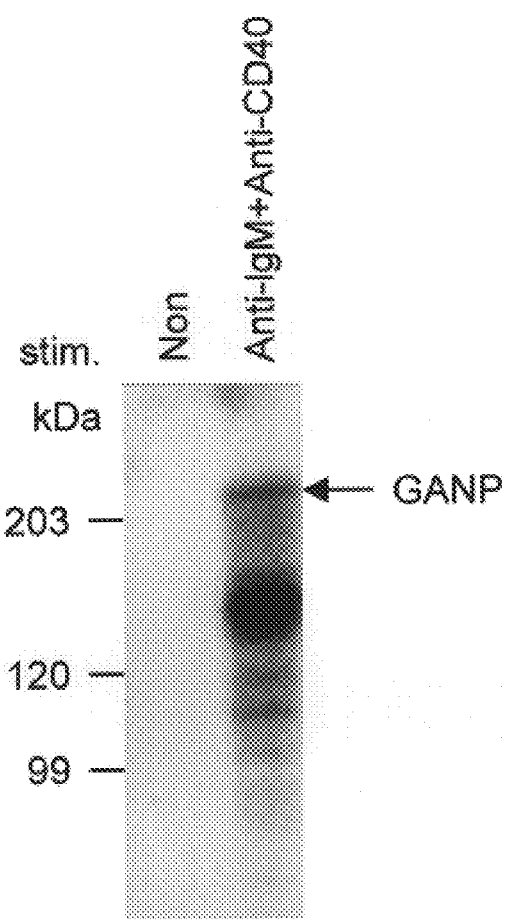
FIG. 17 shows a result of in vitro kinase reaction. The call lysate was prepared from unstimulated (left) or stimulated (right) cells and subjected to anti-GNAP immunoprecipitation. In vitro kinase reaction was carried out with the anti-GNAP (42-23) immunoprecipitates in the presence of [γ-$^{32}$P]-ATP for 10 minutes. Phosphorylation on the proteins was detected by the autoradiography after SDS-PAGE separation. An arrow indicates the position of phosphorylated GNAP.
Figure 18:
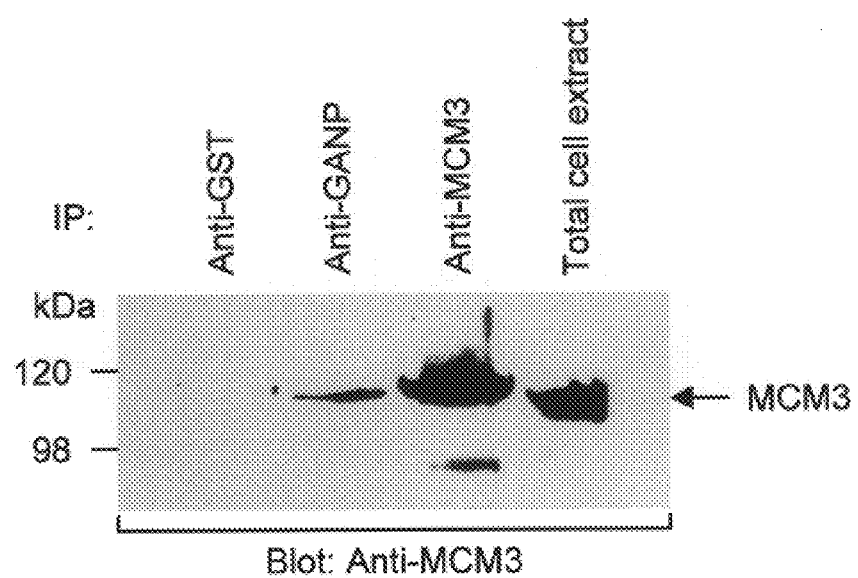
FIG. 18 is a scheme showing a physical association between GNAP and MCM3. The cell lysate from WEHI-231 was immunoprecipitated with anti-GST, anti-GNAP (42-23), or anti-MCM3 Ab. After separation by SDS-PAGE, the proteins were electrophoretically transferred to a membrane and probed with anti-MCM3 Ab.

Since the 210-kDa GANP has many possible phosphorylation sites, we examined the induction of phosphorylation by an in vitro kinase reaction with anti-GANP immunoprecipitates. As shown in FIG. 17, phosphorylation of the 210-kDa protein was found in the anti-GANP immunoprecipitates from spleen B cells stimulated by anti-$\mu$ and anti-CD40 co-ligation. This result indicates that a kinase activity is maintained even if GANP is precipitated.

(7) Association of GANP With MCM3 Protein

Figure 19:
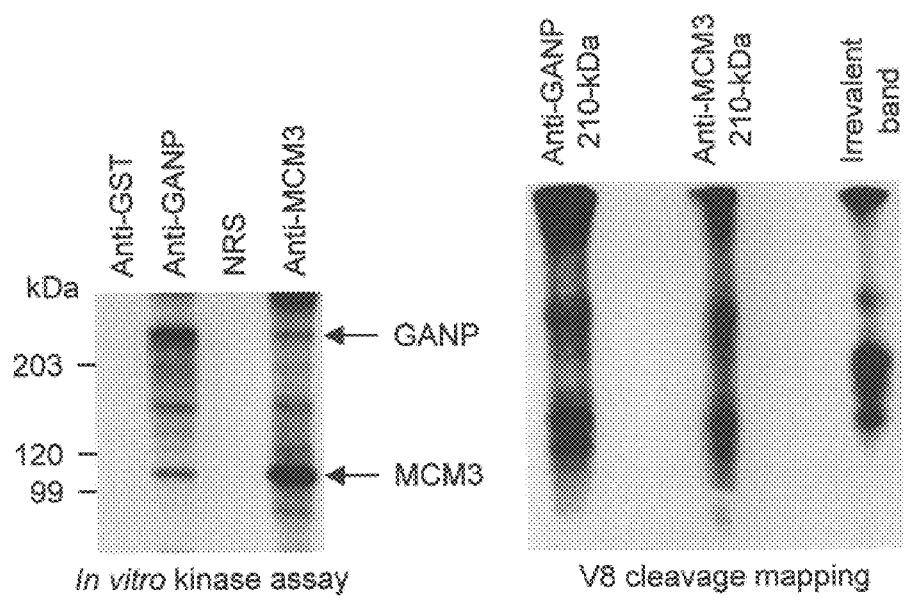
FIG. 19 is a scheme showing a physical association between GNAP and MCM3. Anti-GST, anti-GNAP (42-23) and anti-MCM3 immunoprecipitates from WEHI-231 cell lysates were subjected to in vitro kinase assay. Normal rabbit serum (NRS) was used as a control for anti-MCM3 Ab. The samples were separated by 7% SDS-PAGE. The bands corresponding to GNAP and MCM3 were indicated by arrows in the left panel. On the right panel, V8 cleavage mapping of 210-kDa bands showed an identical cleavage pattern. As a control an irrelevant V8-digested protein was separated in parallel.

We found a Map80-homologous region (76.3% identity at amino acid level) in the carboxyl-terminal part of GANP. Map80 is an 80-kDa nuclear protein that is involved in the translocation of MCM3 (a protein essential for DNA replication) between the cytoplasm and the nuclei (Takei, Y et al, 1998, J. Biol. Chem. 273:22177–22180; Kimura, H. et al, 1994, EMBO J. 13:4311–4320; Chong, J. P. et al, 1996, Trends Biochem Sci. 21:102–106; and Romanowski, P et al, 1996, Curr. Biol. 6:1416–1425). Therefore, we examined the interaction between GANP and MCM3 in WEHI-231. We detected that anti-GANP immunoprecipitates include MCM3. Because the phosphorylation states of MCM proteins seem crucial in regulation of cell cycle progression (Kimura, H. et al, 1994, EMBO J. 13:4311–4320; Chong, J. P. et al, 1996, Trends Biochem Sci. 21:102–106; and Romanowski, P et al, 1996, Curr. Biol. 6:1416–1425), in vitro kinase assays with anti-MCM3 immunoprecipitates was performed. Immunoprecipitation of MCM3 co-precipitated a phosphorylated protein migrated at 210-kDa, which is the identical size of GANP (FIG. 19, left panel). These 210-kDa bands from anti-GANP and anti-MCM3 immunoprecipitates showed an identical pattern in the V8 cleavage mapping (FIG. 19, right panel), indicating that GANP and MCM3 are associated in a B cell line.

Next, we studied whether MCM3 is upregulated in GC-B cells by antigen-immunization of mice in vivo. The contiguous sections to those used above were stained with the anti-MCM3 Ab (FIG. 20). MCM3 is also upregulated in GCs. Double staining clearly demonstrates the co-localization of both MCM3 and PNA. A part of GC area is surrounded intensely with FDCs (lymph follicular cells). These results demonstrate that MCM3 is upregulated in GC-B cells including centroblasts and the GANP$^+$ centrocytes that would be mostly surrounded by FDCs (FIG. 20).

(8) Discussion

As mentioned above, the present inventors found a novel protein, GANP, expressed in GC-B cells localized at the light zone of secondary follicles in the spleen. Although a trace amount of the ganp mRNA is detectable in many kinds of cells under normal conditions, the GANP protein appears upregulated in the specified GC area of immunized mice. A number of studies demonstrated various differentiation antigens in the GC as molecules recognized with mabs or by specific cDNA cloning (Christoph et al., Int. Immunol. 6:1203–1211, 1994; Li et al., Proc. Natl. Acad. Sci. USA. 93:10222–10227, 1996; Kuo et al., J. Exp. Med. 186:1547–1556, 1997). Most molecules appear in GC-B cells of the whole area, whereas 8-oxoguanine DNA glycosylase is expressed in the dark zone (Kuo et al., J. Exp. Med. 186:1547–1556, 1997).

Interestingly, the GANP antigen is selective in the centrocyte of the light zone. Recent studies have shown that RAG protein which is necessary for rearrangement of immunoglobulin gene is selectively expressed in centrocytes at the light zone (Hikida et al., 1996. Science (Washington D.C.) 274:2092–2094, 1996; Han et al., Science (Washington D.C.) 274:2094–2097, 1996). Since the GC area probably provides the site for secondary Ig gene rearrangement occurring during T cell-dependent antibody responses, as described by Papavasiliou et al. and Han et al. (Papavasiliou et al., Science (Washington D.C.), 278:298–301, 1997; Han et al., Science (Washington D.C.), 278: 301–305, 1997), the GANP protein might be a component associated with the maturation of antigen-specific B cells at the centrocyte stage.

We found that the carboxyl-terminal portion of GANP has a significant similarity to human Map80, which facilitates the nuclear transport of MCM3 (Takei, Y et al., 1998, J. Biol. Chem.273:22177–22180). Immunoprecipitation experiments demonstrated that GANP also binds to MCM3 in WEHI-231. MCM3 is a member of the MCM protein family essential for the initiation of DNA replication (Kimura, H. et al, 1994, EMBO J. 13:4311–4320; Blow, J. J. 1993. J. Cell Biol.122.993–1002; Tye, B. K. 1994. Trends Cell Biol. 4: 160–166; Chong, J. P. et al, 1996, Trends Biochem Sci. 21:102–106; Romanowski, P et al, 1996, Curr. Biol. 6:1416–1425; and Thommes, P et al, 1992, Nucl. Acids Res. 20: 1069–1074). The major fractions of nuclear MCM proteins bind to chromatin at the beginning of the S phase, but dissociate during replication and accumulate as free proteins in the nucleosol. The release of MCMs from chromatin is accompanied by the phosphorylation of several MCM proteins and their reassociation after mitosis is concomitant with their dephosphorylation. It was suggested that MCM proteins are no longer synthesized in growth arrested, differentiating cells and disappear with kinetics related to their half-life (Musahl, C., et al, 1998, Exp. Cell. Res. 241, 260–264). The MCM3 protein has recently been shown to an early target in apoptotic proteolysis (Schwab, B. L. et al., 1998, Exp. Cell Res. 238:415–421). Schwab, B. L. et al proposed that active destruction of MCM3 inactivates the MCM complex and serves to prevent untimely DNA replication events during the execution of the cell death program. Our results showed that GC-B cells express high level of MCM3, some of which is associated with GANP. However, it appears curious that a protein, upregulated in differentiated cells that arrest the cell cycle, binds to another protein essential for progression of the S phase. One possible speculation is that a function of GANP may be inactivation of MCM3 through its binding. The immunohistochemistry data are consistent with the following idea; GANP is upregulated in growth-arrested centrocytes while MCM3 is expressed both in rapid-cycling centroblasts and still in centrocytes in GCs. Although the amount of MCM3 would decrease by ceasing the gene expression and active destruction (Musahl, C., et al, 1998, Exp. Cell. Res. 241, 260–264; and Schwab, B. L. et al., 1998, Exp. Cell Res. 238:415–421), inactivation of MCM3, which is still expressed in centrocytes, through the interaction with GANP could be another mechanism to prevent DNA replication. In addition, both GANP and MCM3 become phosphorylated with the co-precipitated kinase (FIG. 19). Since the highly phosphorylated MCM3 is thought to be inactivated form (Kimura, H. et al, 1994, EMBO J. 13:4311–4320), the association with GANP may stimulate phosphorylation of MCM3.

Figure 10:
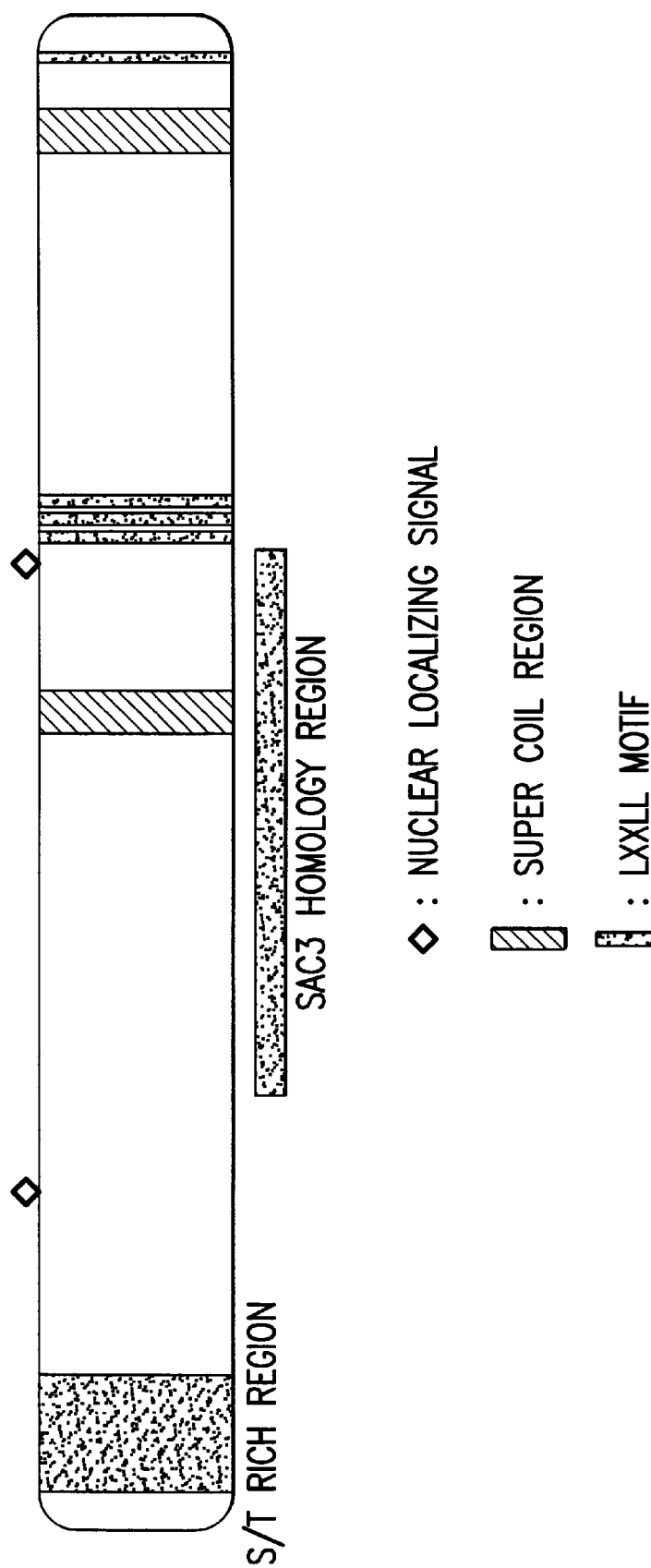
FIG. 10 is a diagram showing a structure of the GANP protein. In the figure, S/T rich region: serine/threonine rich region, SAC3 homology region; SAC3 homology region, nuclear localizing signal: nuclear localizing signal. Four LXXLL motifs are present.

The GANP protein has a close similarity to the SAC3 (SAC, suppressor of actin) of yeasts, *Saccharomyces cerevisiae*, which was isolated in a genetic screen for suppressors of a temperature-sensitive mutation (act1-1) in the actin gene (FIG. 10; Novick et al., Genetics, 121:659–674, 1989). The SAC3 protein is expressed in the nuclei and is required for normal progression of mitosis and protection against the loss of chromosomes (Bauer et al., J. Cell. Sci. 109:1575–1583, 1996). Null mutants of SAC3 grow very slowly and are larger than wild-type cells. SAC3 participates in a process that affects both the actin cytoskeleton and mitosis, which suggest that SAC3 regulates the gene expression of actin or actin-binding proteins.

A gene (named LEP-1) that augments the transcription of the leucine permease activity in Saccharomyces was identical to SAC3 (Stella et al., Yeast 11:460–460, 1995). Although the LEP-1 gene induces the upregulation of the yeast leucine permease involved in selective amino acid transport, the amino acid transport in eukaryotic cells, especially the molecules involved in amino acid permeation is not known (Mastroberardino et al., Nature (Lond.) 395:288–291, 1998). Although the SAC3/LEP-1 sequence does not show motifs homologous to a number of transcription factors, the biological functions determined previously (Bauer et al., J. Cell. Sci. 109:1575–1583, 1996) suggest its regulatory activity of various target genes in the nucleus. The mouse GANP does not show typical consensus motifs for nuclear transcription factors, but has a common ancestor with SAC3 gene of yeasts and has structural similarity of possible phosphorylation sites, two nuclear localization sequences, and two super coil structures that might interact with other transcription molecules.

GANP is selectively upregulated in centrocytes of Ag-immunized spleen. It is also useful as the differentiation marker to define the centrocyte subset that is closely interacting with FDCs in GC area. Our study showed that the BCR signal and the CD40 co-stimulation together cause the upregulation of GANP and lead to the signal transduction mediated through GANP/MCM3 complex.

The defective gene in the autosomal recessive genetic disease autoimmune polyendocrinopathy (APECED) is localized by linkage analysis to human chromosome 21 (21q22.3), which encodes an AIRE gene product with a possible transcription regulator (Nagamine et al., Nature Genet. 17:393–398, 1997). The autoantibody recognizes the AIRE protein expressed in the adrenal gland and other gonad-producing tissues. Studies of APECED drew an idea that the involvement of molecules with nuclear coactivator activity might be associated with the autoimmunity. Both the AIRE and GANP proteins do not have typical domains for transcription regulators, but they have LXXLL motifs as similarly observed in nuclear transcriptional coactivators.

A B cell-specific nuclear coactivator (Bob1/OCA-B/OBF1) was recently characterized as a cell-type-specific regulator of Oct1 and Oct2 (Luo et al., Mol. Cell. Biol. 15:4115–4124, 1995). The OCA-B targeted mice show the impairment of the GC formation in the spleen after immunization with T-dependent antigen, which suggests the functional involvement of B cell maturation in the GC area (Kim et al., Nature (Lond.) 383:542–547, 1996; Qin et al., EMBO J. 17:5066–5075, 1998). The expression of the GANP protein might be under the control of the OCA-B cell in centrocytes. The molecular interaction of the nuclear coactivator molecules would be an important issue for the understanding of the B cell maturation in the GC.

The New Zealand model of SLE has been the experiment subject of genome linkage studies to map the chromosomal positions of disease-susceptibility genes. At least 12 non-MHC loci linked with nephritis and autoantibody production such as on chromosome 4 (designated Nba1), on chromosome 7, and on chromosome 1 (designated as Nba2; Vyse et al., J. Immunol. 158:5566–5574, 1997) have been independently mapped. The GANP antigen on large cells is highly upregulated in the red pulp area of the nonimmunized NZB mice (FIGS. 4–8). NZB mice contained similar large lgM-producing cells, named Mott cells, in the red pulp area. Mott cells appear selectively in NZB and $(NZB \times NZW)F_1$ mice, but not in normal BALB/c or C57BL/6 mice.

The precursor cells of Mott cells are probably B-1 B cells (Tarlinton et al., Eur. J. Immunol. 22:531–539, 1992; Jiang et al., J. Immunol. 158:992–997, 1997), which suggests a close association with the autoimmunity of B cells. Mott cells are apparent with the inclusion body of lgM in the cytoplasm and positive staining with PAS (Tarlinton et al., Eur. J. Immunol. 22:531–539, 1992; Jiang et al., J. Immunol. 158:992–997, 1997). Because GANP$^{dense+}$ cells seem to be Mott cells, PAS staining was performed. However, GANP$^{dense+}$ cells in the red pulp area of NZB mice are PAS$^-$. The GANP$^{dense+}$ lgM-producing cells appear in the spleen of NZB mice, as do Mott cells, but these cells are different. The new type of lgM-producing cells could be generated by the possible activation of an abnormal B cell population related to one of the chromosomal loci linked to disease-susceptibility.

Lyn$^{-/-}$ mice and CD40L$^{-/-}$ mice reported from several laboratories show similar autoimmunities and hyper-lgM syndrome(s), which have an increased appearance of immunoblast cells with the inclusion body in the spleen (Hibbs et al., Cell 83:301–311, 1995; Nishizumi et al., Immunity 3:549–560, 1995; Xu et al., Immunity 1:423–431, 1994). These observations suggest that the signal transduction through BCR and CD40 is regulating the generation of the abnormal antibody-producing plasma cells. Stimulation of splenic B cells with anti-lgM and anti-CD40 antibodies induces the phosphorylation activity of the GANP protein. This observation suggests that the GANP protein may be involved in downstream of the B cell activation site in the GC area and the abnormal B cell activation in NZB mice might be associated with the increased expression of GANP protein.

Example 2

Cloning of Human GANP Gene

On the basis of information of the sequence of rat GANP gene, human GANP gene was cloned and sequenced. Specifically, λgt11-human heart cDNA library (Clontech) was used, and gsp1-1: TTTGTCTGGAGGATGATCGC (SEQ ID No.7 of the sequence listing), gsp1-2: AAA-GAGAAAGGGGCCAGGCC (SEQ ID No.8 of the sequence listing) and gsp1-3: CCAGCTTCTTGTC-CAAAAGC (SEQ ID No.9 of the sequence listing) were used as primers, and 5' RACE System for Rapid Amplification of cDNA Ends, Version 2.0(Gibco BRL) was used to carry out the cloning and sequencing by a conventional method.

The base sequence of the obtained clone was determined. The base sequence of the obtained human GANP gene is shown in SEQ ID No.4 of the sequence listing. The amino acid sequence encoded by this base sequence is shown in SEQ ID No.3 of the sequence listing and FIG. 21. Human GANP gene shows high homology with mouse GANP gene, and Human GANP contains Map80 domain of 80 kDa at carboxyl terminal.

In in situ RNA hybridization, ganp transcript seems to be activated at GC region of tonsil. $GANP^+$ cells express $CD38^+IgD^+$ phenotype of memory B cell. These results show that human GANP is expressed also in GC-B cells of secondary lympho tissues. Moreover, since human GANP of 1980 amino acids has a stretch of Map80 homologous region which binds to MCM3 protein in B cells, it is suggested that GANP is involved in the regulation of cell cycle in GC-B cells.

Figure 22:
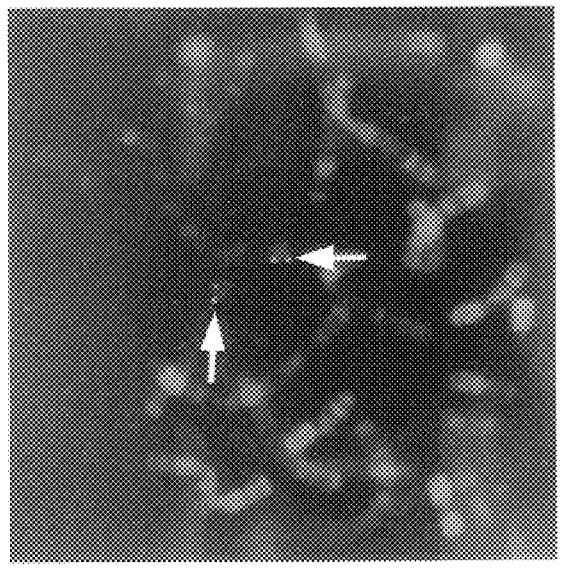
FIG. 22 is a photograph showing a result where human ganp and Map 80 were mapped by FISH method using human chromosome.

Furthermore, in situ hybridization was carried out by FISH method with the obtained human GANP gene and human chromosome specimen. The results are shown in FIG. 22. As is understood from FIG. 22, the genome fragment containing human GANP gene and Map80 was mapped on 22.3 of the long arm of chromosome 21.

Industrial Applicability

The protein of the present invention is a novel protein having a kinase activity, and may be involved in a signal conversion of abnormal B cell differentiation in an autoimmune state. Therefore, the protein, polypeptide, polynucleotide, antisense polynucleotide and antibody of the present invention are useful for revealing the mechanism of autoimmune.

What is claimed:

1. An isolated protein having the amino acid sequence shown in SEQ ID No.3.

2. A polynucleotide which encodes the protein of claim 1.

3. An antisense polynucleotide, which comprises the base sequence of an antisense chain of the polynucleotide of claim 2.

4. A variant protein having a kinase activity substantially similar to the protein recited in claim 1, wherein 1–20 amino acids are deleted, substituted, and/or added.

5. A polynucleotide which encodes the protein of claim 4.

6. An antisense polynucleotide, which comprises the base sequence of an antisense chain of the polynucleotide of claim 5.

* * * * *

UNITED STATES PATENT AND TRADEMARK OFFICE
CERTIFICATE OF CORRECTION

PATENT NO. : 6,673,913 B1　　　　　　　　　　　　　　　　　　　　　　　　Page 1 of 1
APPLICATION NO. : 09/914272
DATED : January 6, 2004
INVENTOR(S) : Sakaguchi et al.

It is certified that error appears in the above-identified patent and that said Letters Patent is hereby corrected as shown below:

On the Title page of the Letters Patent and Under Column 1;

Under section "(54) and Column 1, line 1", change "GANP PROTEINS" to
-- GANP PROTEIN --

Under section "(22) PCT Filed: and Column 1, line 4", change "Aug. 27, 2000" to
-- Aug. 27, 1999 --

Signed and Sealed this

Twentieth Day of January, 2009

JON W. DUDAS
*Director of the United States Patent and Trademark Office*